United States Patent
Nelson et al.

(10) Patent No.: US 7,696,186 B2
(45) Date of Patent: *Apr. 13, 2010

(54) 7,9-SUBSTITUTED TETRACYCLINE COMPOUNDS

(75) Inventors: Mark L. Nelson, Wellesley, MA (US); Roger Frechette, Reading, MA (US); Peter Viski, Brookline, MA (US); Mohamed Y. Ismail, Bedford, MA (US); Todd Bowser, Charlton, MA (US); Laura McIntyre, Arlington, MA (US); Beena Bhatia, Mansfield, MA (US); Paul Hawkins, Cambridge, MA (US); Laxma Reddy, Solon, OH (US); Karen Stapleton, Weymouth, MA (US); Tadeusz Warchol, Northborough, MA (US); Paul Sheahan, San Diego, CA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 559 days.

This patent is subject to a terminal disclaimer.

(21) Appl. No.: 10/738,862

(22) Filed: Dec. 16, 2003

(65) Prior Publication Data

US 2004/0138183 A1 Jul. 15, 2004

Related U.S. Application Data

(63) Continuation of application No. 09/895,797, filed on Jun. 29, 2001, now Pat. No. 6,683,068.

(60) Provisional application No. 60/275,620, filed on Mar. 13, 2001.

(51) Int. Cl.
*A61K 31/65* (2006.01)
*C07C 237/28* (2006.01)

(52) U.S. Cl. .................................. 514/152; 552/203

(58) Field of Classification Search ................ 552/203; 514/152

See application file for complete search history.

(56) References Cited

U.S. PATENT DOCUMENTS

| | | |
|---|---|---|
| 2,980,584 A | 4/1961 | Hammer |
| 2,990,331 A | 6/1961 | Neumann et al. |
| 3,062,717 A | 11/1962 | Hammer |
| 3,165,531 A | 1/1965 | Blackwood et al. |
| 3,226,436 A | 12/1965 | Petisi et al. |
| RE26,253 E | 8/1967 | Petisi et al. |
| 3,338,963 A | 8/1967 | Petisi et al. |
| RE26,271 E | 9/1967 | Boothe et al. |
| 3,341,585 A | 9/1967 | Bitha et al. |
| 3,345,410 A | 10/1967 | Winterbottom |
| 3,373,193 A | 3/1968 | Schroeder et al. |
| 3,403,179 A | 9/1968 | Zambrano |
| 3,433,834 A | 3/1969 | Winterbottom et al. |
| 3,454,697 A | 7/1969 | Joyner et al. |
| 3,483,251 A | 12/1969 | Zambrano |
| 3,518,306 A | 6/1970 | Martell Jr. |
| 3,557,280 A | 1/1971 | Weber et al. |
| 3,579,579 A | 5/1971 | Hlavka et al. |
| 3,674,859 A | 7/1972 | Beutel et al. |
| 3,901,942 A | 8/1975 | Bernardi et al. |
| 3,957,980 A | 5/1976 | Noseworthy |
| 3,988,468 A | 10/1976 | Rogalski et al. ............. 424/275 |
| 3,993,694 A | 11/1976 | Martin et al. |
| 4,018,889 A | 4/1977 | Armstrong |
| 4,024,272 A | 5/1977 | Rogalski et al. |
| 4,126,680 A | 11/1978 | Armstrong |
| 5,248,797 A | 9/1993 | Sum |
| 5,281,628 A | 1/1994 | Hlavka et al. |
| 5,284,963 A | 2/1994 | Sum et al. |
| 5,326,759 A | 7/1994 | Hlavka et al. |
| 5,328,902 A | 7/1994 | Sum et al. |
| 5,371,076 A | 12/1994 | Lee et al. |
| 5,380,888 A | 1/1995 | Sum et al. |
| 5,386,041 A | 1/1995 | Sum et al. |
| 5,401,729 A | 3/1995 | Sum et al. |
| 5,401,863 A | 3/1995 | Hlavka et al. |
| 5,420,272 A | 5/1995 | Sum et al. |
| 5,430,162 A | 7/1995 | Sum et al. |

(Continued)

FOREIGN PATENT DOCUMENTS

| | | |
|---|---|---|
| DE | 2346535 | 4/1974 |
| DE | 2527568 | 1/1976 |
| DE | 2527568 A1 | 1/1976 |
| EP | 0535346 B1 | 4/1993 |
| EP | 0536515 B1 | 4/1993 |
| EP | 0582788 B1 | 2/1994 |
| EP | 0582789 B1 | 2/1994 |
| EP | 0582790 B1 | 2/1994 |
| EP | 0582810 B1 | 2/1994 |
| EP | 0582829 B1 | 2/1994 |

(Continued)

OTHER PUBLICATIONS

Berge, S.M., et al., "Pharmaceutical Salts," *Journal of Pharmaceutical Science*. Jan. 1977;66(1):1-19.

Van den Bogert, C., et al., "Doxycycline in combination chemotherapy of a rat leukemia," *Cancer Research*. Dec. 1, 1988;48(23):6686-90.

(Continued)

*Primary Examiner*—Barbara P Badio
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The present invention pertains to novel 7,9-substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

18 Claims, No Drawings

U.S. PATENT DOCUMENTS

| | | | |
|---|---|---|---|
| 5,442,059 A | 8/1995 | Sum et al. | |
| 5,457,096 A | 10/1995 | Sum et al. | |
| 5,466,684 A | 11/1995 | Sum et al. | |
| 5,494,903 A | 2/1996 | Hlavka et al. | |
| 5,495,018 A | 2/1996 | Sum et al. | |
| 5,495,030 A | 2/1996 | Sum et al. | |
| 5,495,031 A | 2/1996 | Sum et al. | |
| 5,512,553 A | 4/1996 | Sum et al. | |
| 5,529,990 A | 6/1996 | Hlavka et al. | |
| 5,530,117 A | 6/1996 | Hlavka et al. | |
| 5,532,227 A | 7/1996 | Golub et al. | |
| 5,567,692 A | 10/1996 | Sum et al. | |
| 5,567,693 A | 10/1996 | Backer et al. | |
| 5,639,742 A | 6/1997 | Lee et al. | |
| 5,675,030 A | 10/1997 | Krishnan et al. | |
| 5,789,395 A | 8/1998 | Amin et al. | |
| 5,834,450 A | 11/1998 | Su | |
| 5,843,925 A | 12/1998 | Backer et al. | |
| 5,856,315 A | 1/1999 | Backer et al. | |
| 5,886,175 A | 3/1999 | Sum et al. | |
| 6,506,740 B1 * | 1/2003 | Ashley et al. | 514/152 |
| 6,617,318 B1 * | 9/2003 | Nelson et al. | 514/152 |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,683,365 B1 | 1/2004 | Trivedi | |
| 6,818,634 B2 | 11/2004 | Nelson et al. | |
| 6,841,546 B2 | 1/2005 | Draper et al. | |
| 2002/0103171 A1 | 8/2002 | Nelson et al. | |
| 2002/0111335 A1 | 8/2002 | Nelson et al. | |
| 2002/0115644 A1 | 8/2002 | Levy et al. | |
| 2002/0123637 A1 | 9/2002 | Levy et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2002/0160987 A1 | 10/2002 | Ashley et al. | |
| 2003/0055025 A1 | 3/2003 | Nelson et al. | |
| 2003/0125348 A1 | 7/2003 | Nelson et al. | |
| 2003/0166585 A1 | 9/2003 | Draper et al. | |
| 2003/0195174 A1 | 10/2003 | Ashley et al. | |
| 2004/0002481 A1 | 1/2004 | Ashley et al. | |
| 2004/0063674 A1 | 4/2004 | Levy et al. | |
| 2004/0067912 A1 | 4/2004 | Hlavka et al. | |
| 2004/0092490 A1 | 5/2004 | Draper et al. | |
| 2004/0157806 A1 | 8/2004 | Nelson et al. | |
| 2004/0176334 A1 | 9/2004 | Nelson et al. | |

FOREIGN PATENT DOCUMENTS

| | | |
|---|---|---|
| EP | 0618190 B1 | 10/1994 |
| GB | 921252 | 3/1963 |
| GB | 1 413 347 | 11/1975 |
| GB | 1469384 | 4/1997 |
| WO | WO-96/34852 A1 | 11/1996 |
| WO | WO-99/37306 A1 | 7/1999 |
| WO | WO 00/28983 A1 | 5/2000 |
| WO | WO-01/19784 A1 | 3/2001 |
| WO | WO-01/74761 A1 | 10/2001 |
| WO | WO-01/87824 A2 | 11/2001 |
| WO | WO-01/98259 A1 | 12/2001 |
| WO | WO-02/04406 A2 | 1/2002 |
| WO | WO-02/04407 A2 | 1/2002 |

OTHER PUBLICATIONS

Sum, P.E., et al., "Synthesis and Structure-activity Relationship of Novel Glycylcycline Derivatives Leading to the Discovery of GAR 936." *Bioorganic & Medicinal Chemistry Letters*. 1999: 9(10)1459-62.

Barden, Timothy C., et al., "'Glycylcyclines.' 3. 9-Aminodoxycyclinecarboxamides," *J. Med. Chem.*, vol. 37:3205-3211 (1994).

Koza, Darrell, J., et al., "Synthesis and Biological Evaluation of 9-Substituted Tetracycline Derivatives," *Bioorganic & Medicinal Chemistry Letters*, vol. 12:2163-2165 (2002).

Koza, Darrell, J., et al., "Palladium Catalyzed C-N Bond Formation in the Synthesis of p7-Amino-Substituted Tetracyclines," *J. Org. Chem.*, vol. 67:5025-5027 (2002).

Koza, Darrell, J., "Synthesis of 7-Substituted Tetracycline Derivatives," *Organic Letters*, vol. 2(6):815-817 (2000).

Petersen, P.J., et al., "In Vitro and in Vivo Antibacterial Activities of a Novel Glycylcycline, the 9-*t*-Butylglycylamido Derivative of Minocycline (GAR-936)," *Antimicrobial Agents and Chemotherapy*, vol. 43(4):738-744 (1999).

Spencer, John L., et al., "6-Deoxytetracyclines. V.1a 7,9-Disubstituted Products," *J. Med. Chem.*, vol. 122:405-407 (1963).

Sum, Phaik-Eng, et al., "Glycylcyclines. 1. A New Generation of Potent Antibacterial Agents through Modification of 9-Aminotetracyclines," *J. Med. Chem.*, vol. 37:184-188 (1994).

Sum, Phaik-Eng, et al., "Synthesis and Structure-Activity Relationship of Novel Glycylcycline Derivatives Leading to the Discovery of GAR-936," *Bioorganic & Medicinal Chemistry Letters*, vol. 9:1459-1462 (1999).

Sum, P.E., et al., "Recent developments in tetracycline antibiotics," *Curr. Pharm. Des.*, vol. 4(2):119-132 (1998).

Tally, F.T., et al.l., "Glycylcyclines: a new generation of tetracyclines," *Journal of Antimicrobial Chemotherapy*, vol. 35:449-452 (1995).

Chemical Abstract, Bernardi, Luigi, et al., "Alkyltetracyclines and tetracycline derivatives," May 12, 1984.

Chemical Abstract, Bernardi, Luigi, et al., "Tetracycline derivatives," May 12, 1984.

Chemical Abstract, Sum, Phaik-Eng, et al., "Synthesis and structure-activity relationship of novel glycylcycline derivatives leading to the discovery of GAR-936," Jun. 8, 1999.

Chemical Abstract, Backer, Joseph W., et al., "Methods using 7-(substituted amino)-9-([substituted glycyl] amido]-6-demethyl-6-deoxytetracyclines for inhibiting angiogenesis, proliferation of endothelial or tumor cells, and tumor growth," Dec. 15, 1998.

Chemical Abstract, Krishnan, Lalitha, et al., "Method for selective extracting a 7-(hydrogen or substituted amino)-9-[ (substituted glycyl) amido]-6-demethyl-6-deoxytetracycline compound," Oct. 16, 1997.

Chemical Abstract, Backer, Joseph M., et al., "Method for inhibiting angiogenesis, proliferation of endothelial or tumor cells and tumor growth," Nov. 7, 1996.

* cited by examiner

7,9-SUBSTITUTED TETRACYCLINE COMPOUNDS

RELATED APPLICATIONS

This application is a continuation application of U.S. application Ser. No. 09/895,797 filed Jun. 29, 2001, now U.S. Pat. No. 6,683,068, issued Jan. 27, 2004, entitled "7,9-Substituted Tetracycline Compounds", which claims priority to U.S. Provisional Patent Application Ser. No. 60/275,620, entitled "7,9-Substituted Tetracycline Compounds", filed on Mar. 13, 2001. Each of the aforementioned application and patent are hereby incorporated herein by reference in their entirety.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice.

SUMMARY OF THE INVENTION

In an embodiment, the invention pertains to 7,9-substituted tetracycline compounds of Formula I:

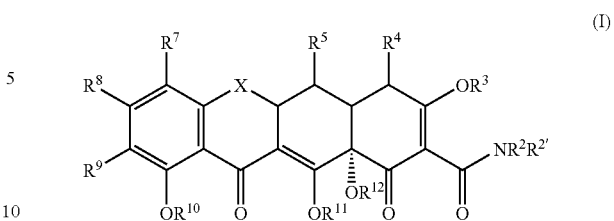

wherein:

X is $CHC(R^{13}Y'Y)$, $CR^{6'}R^{6}$, S, $NR^{6}$, or O;

$R^{2}$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{4}$ is $NR^{4'}R^{4''}$, alkyl, alkenyl, alkynyl, hydroxyl, halogen, or hydrogen;

$R^{2'}$, $R^{3}$, $R^{10}$, $R^{11}$ and $R^{12}$ are each hydrogen or a pro-drug moiety;

$R^{5}$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^{6}$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^{7}$ is nitro, alkyl, alkenyl, alkynyl, aryl, alkoxy, alkylthio, alkylsulfinyl, alkylsulfonyl, arylalkyl, amino, arylalkenyl, arylalkynyl, or $-CH_{2})_{0-3}NR^{7c}C(=W')WR^{7a}$;

$R^{9}$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-CH_{2})_{0-3}NR^{9c}C(=Z')ZR^{9a}$;

Z is $CR^{9d}R^{9e}$, S, $NR^{9b}$ or O;

Z' is O, S, or $NR^{9f}$;

W is $CR^{7d}R^{7e}$, S, $NR^{7b}$ or O;

W' is O, $NR^{7f}$,S;

$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{8}$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains to a method for treating a tetracycline responsive state in a subject, by administering to the subject a tetracycline compound of the invention (e.g., of Formula I), such that the tetracycline responsive state is treated.

DETAILED DESCRIPTION OF THE INVENTION

The present invention pertains, at least in part, to novel 7,9-substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline. Other derivatives and analogues comprising a similar four ring structure are also included. Table 1 depicts tetracycline and several known tetracycline derivatives.

TABLE I

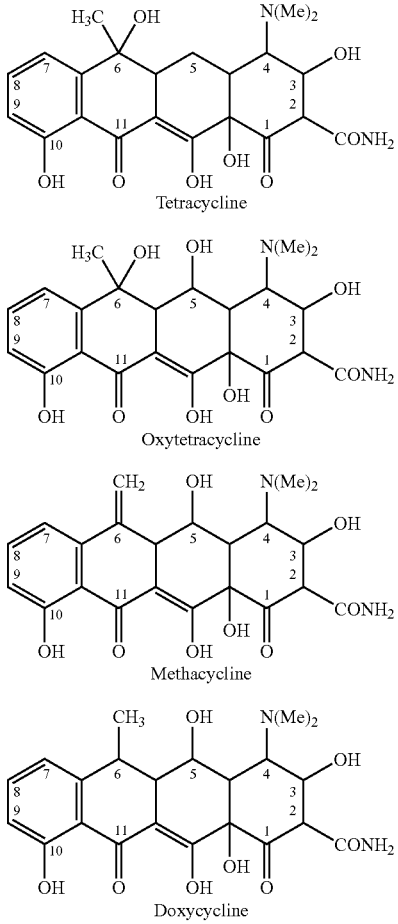

Tetracycline

Oxytetracycline

Methacycline

Doxycycline

The term "7,9-substituted tetracycline compounds" includes tetracycline compounds with substitution at the 7 and 9-positions. In one embodiment, the substitution at the 7- and 9-positions enhances the ability of the tetracycline compound to perform its intended function, e.g., treat tetracycline responsive states. In an embodiment, the 7,9-substituted tetracycline compound is 7,9-substituted tetracycline (e.g., wherein $R^4$ is $NR^{4'}R^{4''}$; $R^{4'}$ and $R^{4''}$ are methyl, $R^5$ is hydrogen and X is $CR^6R^{6'}$, wherein $R^6$ is methyl and $R^{6'}$ is hydroxy); 7,9-substituted doxycycline (e.g., wherein $R^4$ is $NR^{4'}R^{4''}$; $R^{4'}$ and $R^{4''}$ are methyl, $R^5$ is hydroxyl and X is $CR^6R^{6'}$, wherein $R^6$ is methyl and $R^{6'}$ is hydrogen); or 7,9-substituted sancycline (wherein $R^4$ is $NR^{4'}R^{4''}$; $R^{4'}$ and $R^{4''}$ are methyl; $R^5$ is hydrogen and X is $CR^6R^{6'}$ wherein $R^6$ and $R^{6'}$ are hydrogen atoms. In an embodiment, the substitution at the 7 position of the 7,9-substituted tetracycline compound is not chlorine or trimethylamino. In one embodiment, $R^4$ is hydrogen.

The 7,9-substituted tetracycline compounds of the invention include compounds of Formula I:

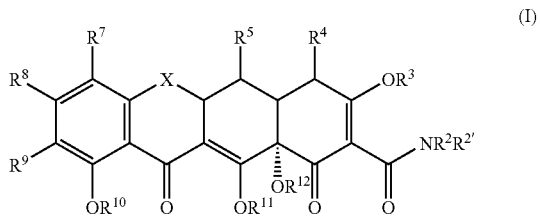

(I)

wherein:
X is $CHC(R^{13}Y'Y)$, $CR^6R^6$, S, $NR^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is nitro, alkyl, alkenyl, alkynyl, aryl, alkoxy, alkylthio, alkylsulfinyl, alkylsulfonyl, arylalkyl, amino, arylalkenyl, arylalkynyl, or $—CH_2)_{0-3}NR^{7c}C(=W')WR^{7a}$;
$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $—CH_2)_{0-3}NR^{9c}C(=Z')ZR^{9a}$;
Z is $CR^{9d}R^{9e}$, S, $NR^{9b}$ or O;
Z' is O, S, or $NR^{9f}$;
W is $CR^{7d}R^{7e}$, S, $NR^{7b}$ or O;
W' is O, $NR^{7f}$ S;
$R^{7a}$, $R^{7b}$, $R^{7c}$, $R^{7d}$, $R^{7e}$, $R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The tetracycline compounds of the invention include, for example, compounds wherein X is $CR^6R^{6'}$; $R^4$ is $NR^{4'}R^{4''}$; $R^2$, $R^{2'}$, $R^6$, $R^{6'}$, $R^8$, $R^{10}$, $R^{11}$, and $R^{12}$ are each hydrogen; $R^{4'}$ and $R^{4''}$ are lower alkyl; and $R^5$ is hydroxy or hydrogen. In an embodiment, $R^{4'}$ and $R^{4''}$ are each methyl and $R^5$ is hydrogen. The tetracycline compounds of the invention include each possible combination of $R^7$ and $R^9$ substituents discussed below.

In an embodiment, $R^7$ is aryl (e.g., heteroaryl or substituted or unsubstituted phenyl). The phenyl $R^7$ group may be substituted with one or more substituents. Examples of substituents of phenyl $R^7$ groups include alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituent is substituted or unsubstituted alkyl (e.g., methyl, ethyl, propyl, butyl, etc.), nitro, halogen (e.g., fluorine, bromine, chlorine, iodine, etc.), amino (e.g., unsubstituted amino, alkyl amino, dialkylamino (e.g., dimethylamino), or alkoxy (methylenedioxy or methoxy).

$R^7$ also may be substituted or unsubstituted alkyl(e.g., methyl, ethyl, i-propyl, n-propyl, t-butyl, i-butyl, n-butyl, pentyl, n-pentyl, n-hexyl, or hexyl). The alkyl may be branched or straight chain and may comprise a ring, e.g., a cycloalkyl ring, e.g., cyclohexyl ring.

The alkyl $R^7$ group may be substituted with any substituent which allows the tetracycline compound to perform its intended function. Examples of substituents include, but are not limited to, alkenyl, halogen (e.g., fluorine, chlorine, bromine, iodine, etc.), hydroxyl, alkoxy (e.g., methoxy, ethoxy, perchloromethoxy, perfluoromethoxy, etc.), alkylcarbonyloxy, alkoxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

Examples of heterocyclic substituents include N-isoindole-[1,3]-dione (e.g., phthalimide). In an embodiment, the substituent is arylcarbonylamino, e.g., heteroaryl carbonyl amino. The heteroaryl group may be, for example, pyridinyl. Other examples of substituents include amino or carboxylate.

In another embodiment, $R^7$ is acyl, e.g., acetyl.

In yet another embodiment, $R^7$ is substituted or unsubstituted alkynyl. Examples of substituents include those which allow the tetracycline compound to perform its intended function. Examples of substituents include, but are not limited to, alkyl (e.g., methyl, ethyl, propyl, butyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituent is substituted or unsubstituted phenyl. The phenyl also may be further substituted with one or more substituents which allow the compound to perform its intended function. Examples of phenyl substituents include, but are not limited to, alkoxy (e.g., methoxy).

The tetracycline compounds of the invention include compounds wherein $R^9$ is substituted or unsubstituted aryl (e.g., carbocyclic or heteroaryl). In an embodiment, $R^9$ is substituted or unsubstituted phenyl. The substituted phenyl group can be substituted with any substituent or combination of substituents which allows the compound to perform its intended function. Examples of substituents include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the phenyl $R^9$ substituent is substituted or unsubstituted alkyl, nitro, halogen, amino, or alkoxy (e.g., methylenedioxy).

The invention also includes compounds wherein $R^9$ is substituted or unsubstituted alkyl (e.g., methyl, ethyl, i-propyl, n-propyl, i-butyl, t-butyl, n-butyl, pentyl, hexyl, etc.). The alkyl group may be substituted with any substituent that allows the compound to perform its intended function. Examples of the substituents include, but are not limited to, alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, alkylcarbonylamino, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In an embodiment, wherein said substituent is unsubstituted amino. In a further embodiment, the $R^9$ group is aminomethyl. In another, the alkyl $R^9$ group is substituted with arylcarbonylamino (e.g., heteroarylcarbonylamino, e.g., pyridinylcarboynlamino) or alkylcarbonylamino.

In another further embodiment, the $R^9$ alkyl group is substituted with a heterocyclic substituent, such as isoindole-[1,3]-dione (e.g., phthalimide).

In an embodiment, $R^7$ is acyl, e.g., acetyl.

In yet another embodiment, $R^9$ is substituted or unsubstituted alkynyl. The alkynyl $R^9$ group can be substituted with any substituent which allows the tetracycline compound of the invention to perform its intended function. Examples of substituents include, but are not limited to, alkyl (e.g., methyl, ethyl, propyl, butyl, pentyl, hexyl, heptyl, etc.), alkenyl, halogen, hydroxyl, alkoxy, alkylcarbonyloxy, alkyloxycarbonyl, arylcarbonyloxy, arylcarbonylamino, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl substituted alkynyl $R^9$ moiety is, for example, substituted or unsubstituted phenyl. The phenyl may be substituted with, for example, alkoxy, e.g., methoxy. Examples of alkenyl substituents include cycloalkenes such as, cyclohexene.

In one embodiment, $R^9$ is not unsubstituted phenyl when $R^7$ is unsubstituted phenyl.

Examples of 7,9-substituted tetracycline compounds of the invention include those listed below and in Table 2:

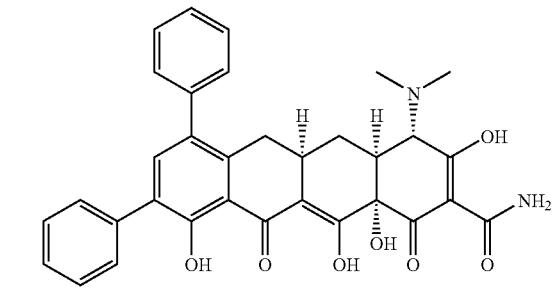

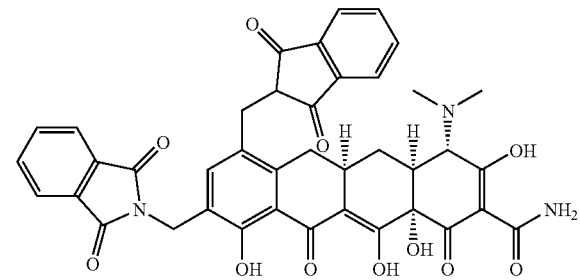

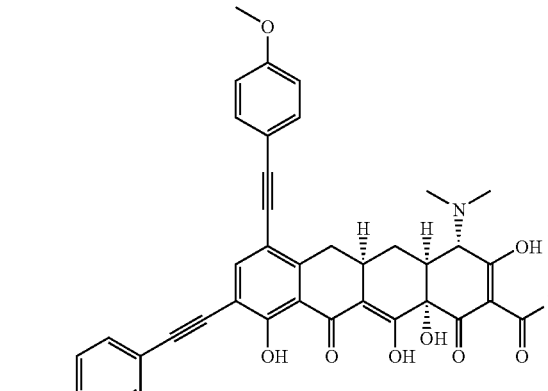

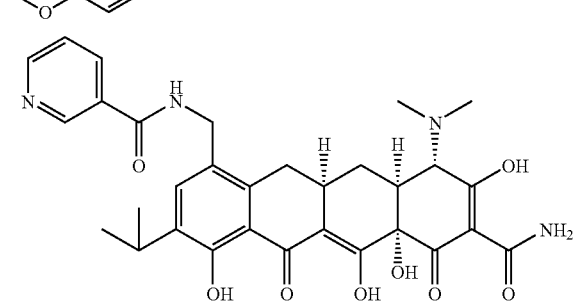

-continued

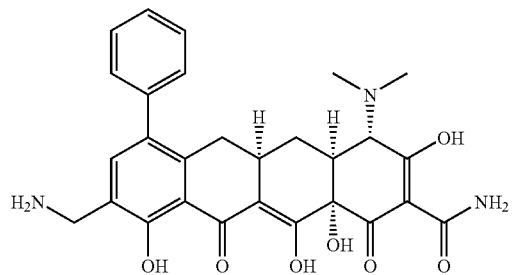

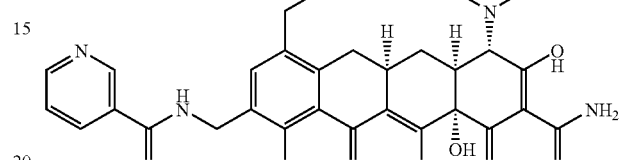

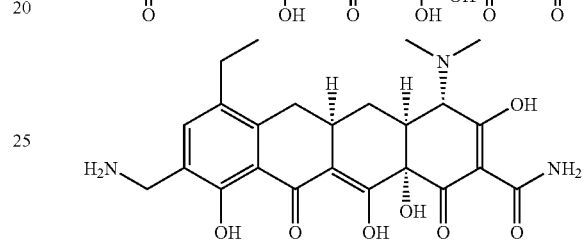

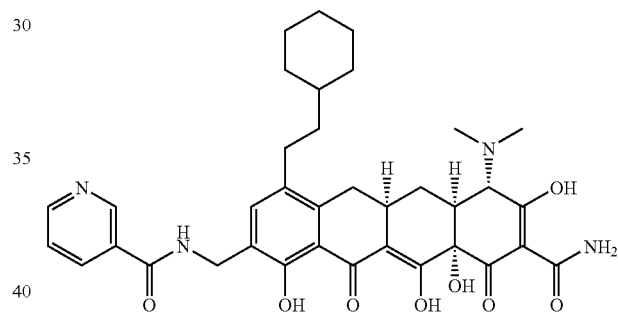

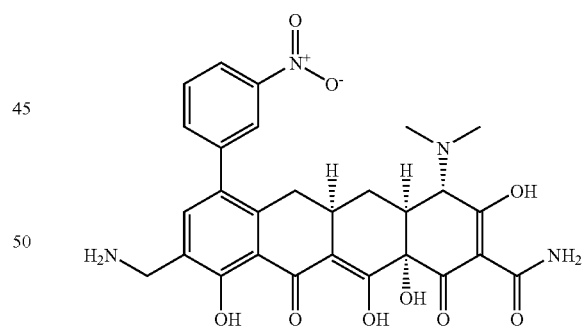

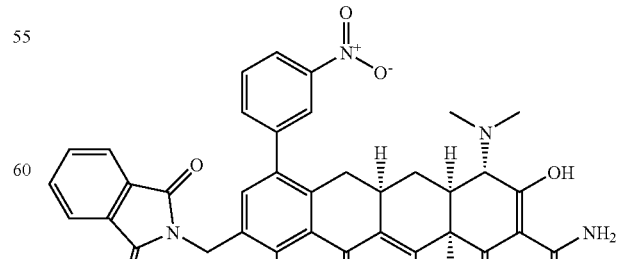

-continued
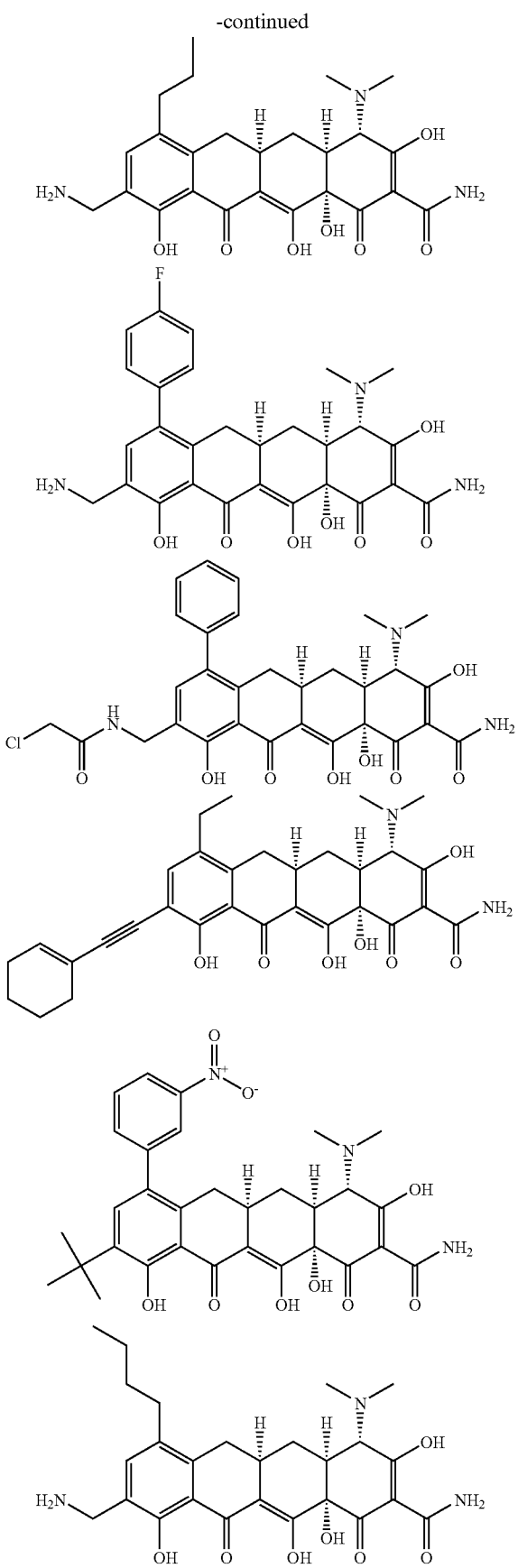
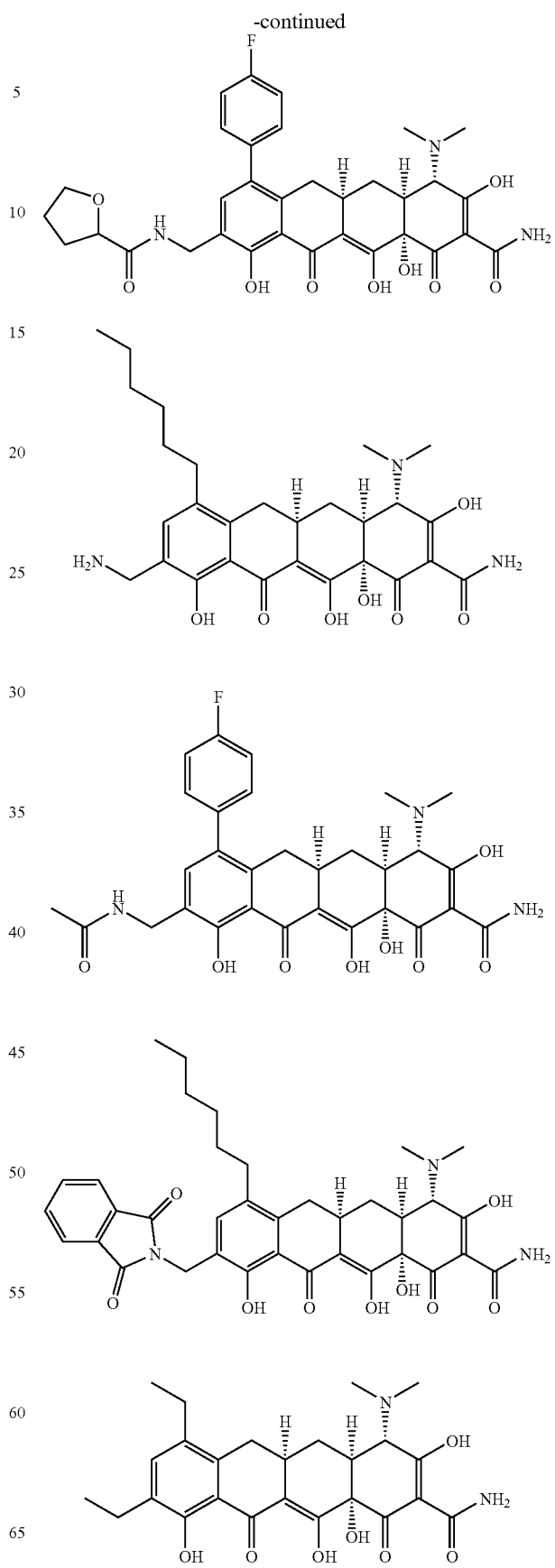

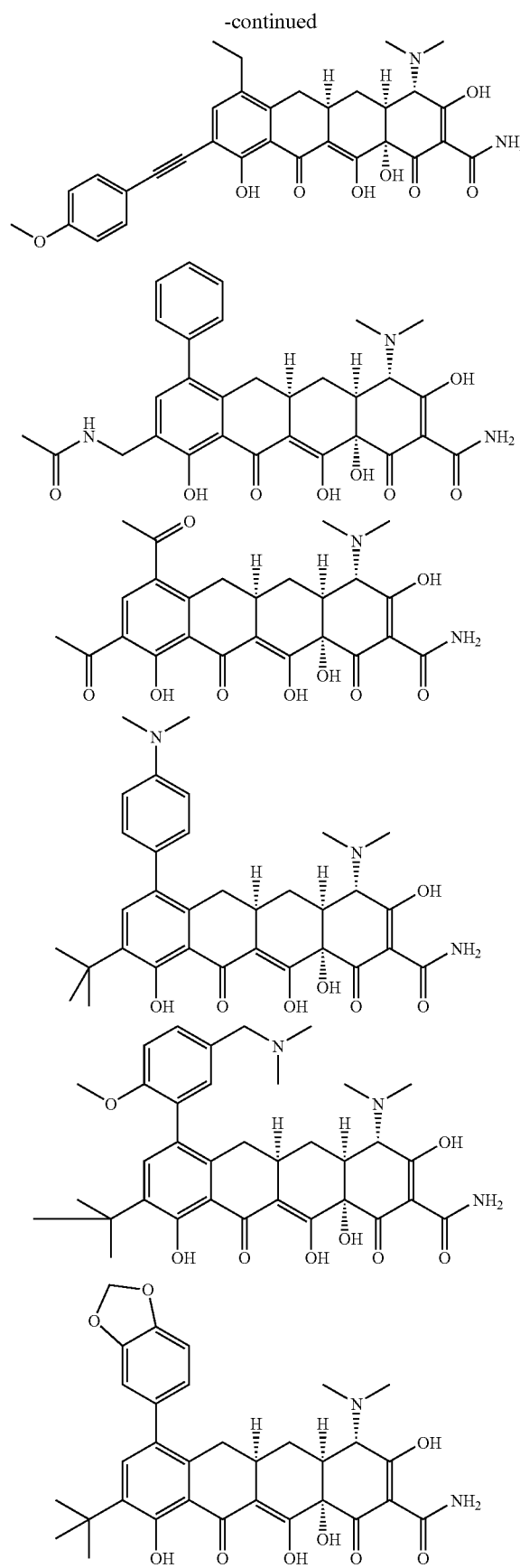

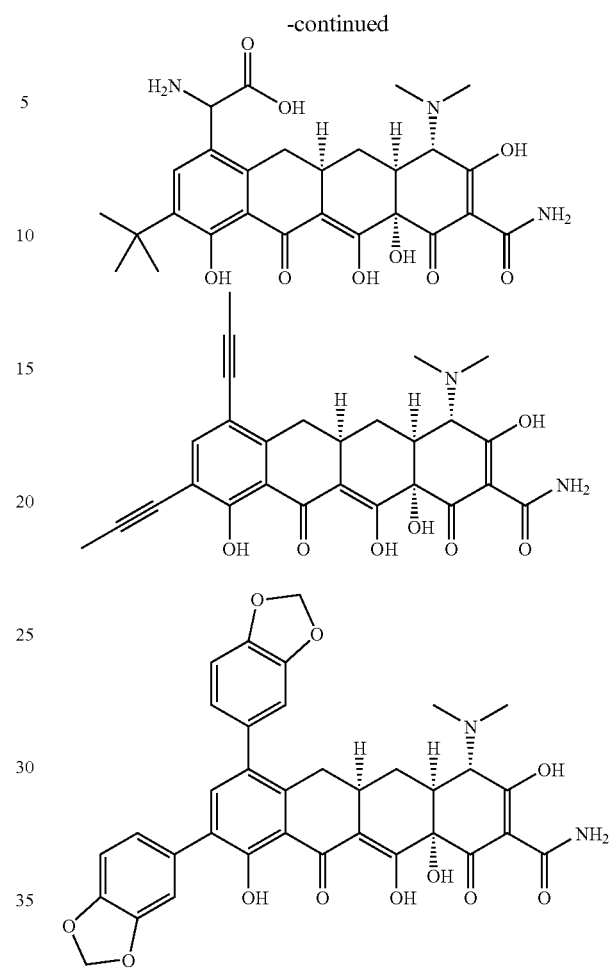

The invention also pertains to each of the 7,9-substituted tetracycline compounds shown in Table 2, as well as their pharmaceutically acceptable salts.

The 7,9-disubstituted tetracycline compounds of this invention can be synthesized using the methods described in Schemes 1-5.

Certain 7,9-substituted tetracycline compounds can be synthesized by the method shown in Scheme 1. Although in each scheme sancycline is used as the tetracycline compound, one of skill in the art will appreciate that the methodology can also be applied to other tetracycline compounds such as tetracycline and doxycycline. Furthermore, some of the following methods are shown for seven substituted compounds. Similar protocols can be followed to substituted the compounds at the 9 position.

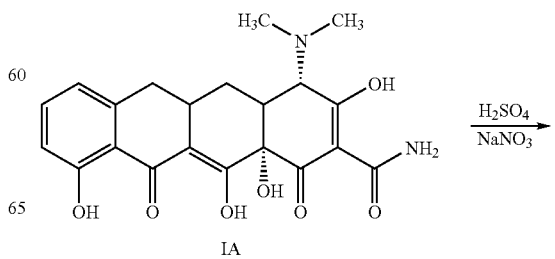

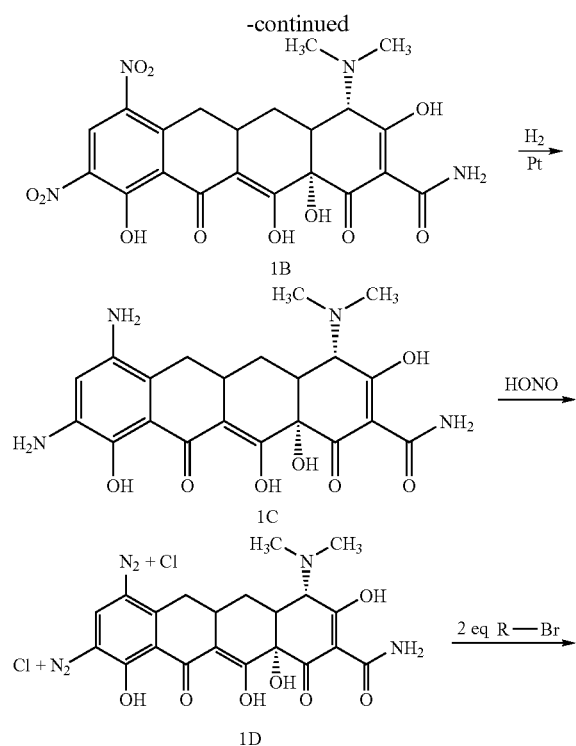
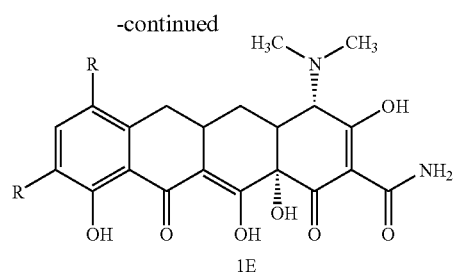

Generally, 7,9-substituted tetracycline compounds can be synthesized as shown in Scheme 1 for sancycline. Sancycline (1A) is treated with sulfuric acid and sodium nitrate. The resulting product is 7,9-nitro (1B) sancycline. The nitro sancycline compound is then treated with hydrogen gas and a platinum catalyst to yield the 7,9-amino sancycline compound, 1C. To synthesize derivatives, the 7,9-amino sancycline compound is treated with HONO, to yield the diazonium salt (1D). The salt can subsequently be treated with numerous compounds possessing an alkene or π bond functional group such as alkenes, aryls, and alkynyls (e.g., RBr) yielding the 7,9-substituted sancycline compound (1E).

SCHEME 2

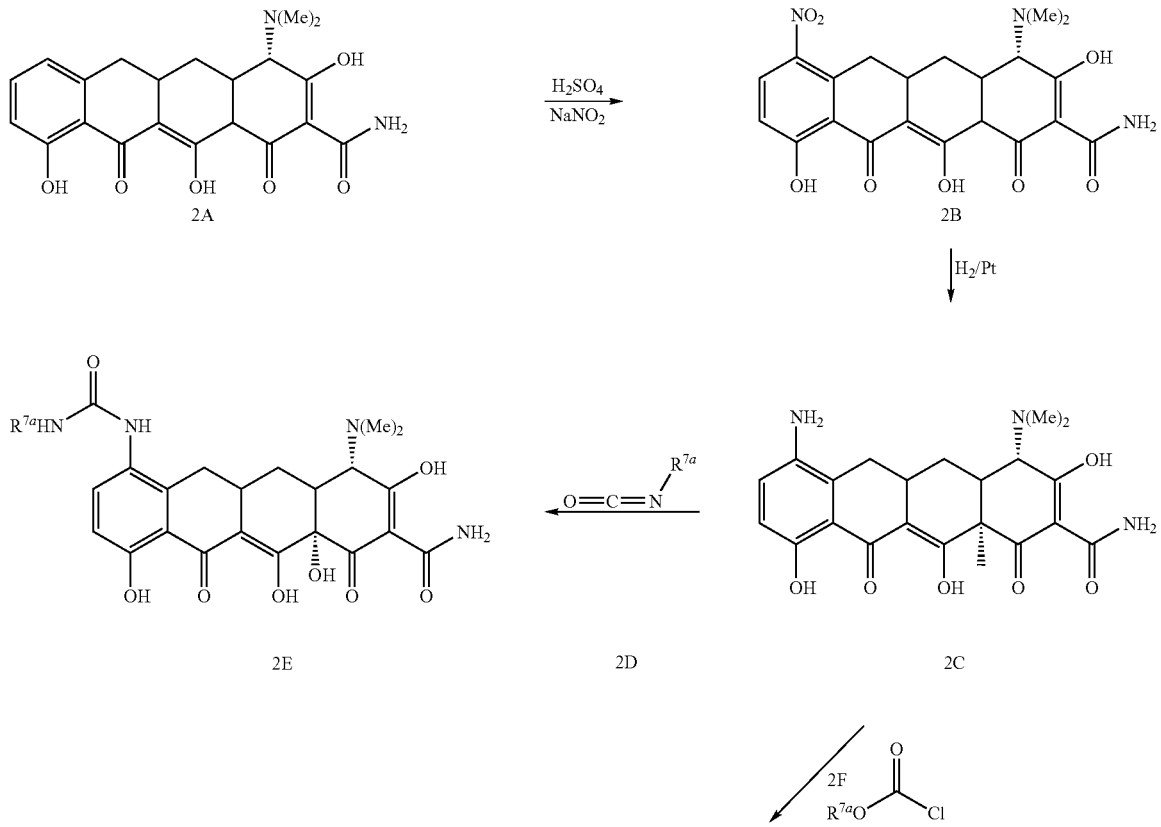

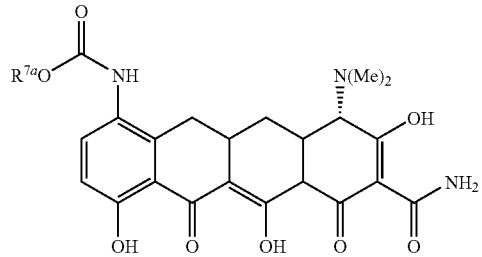

2G

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of 9-positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

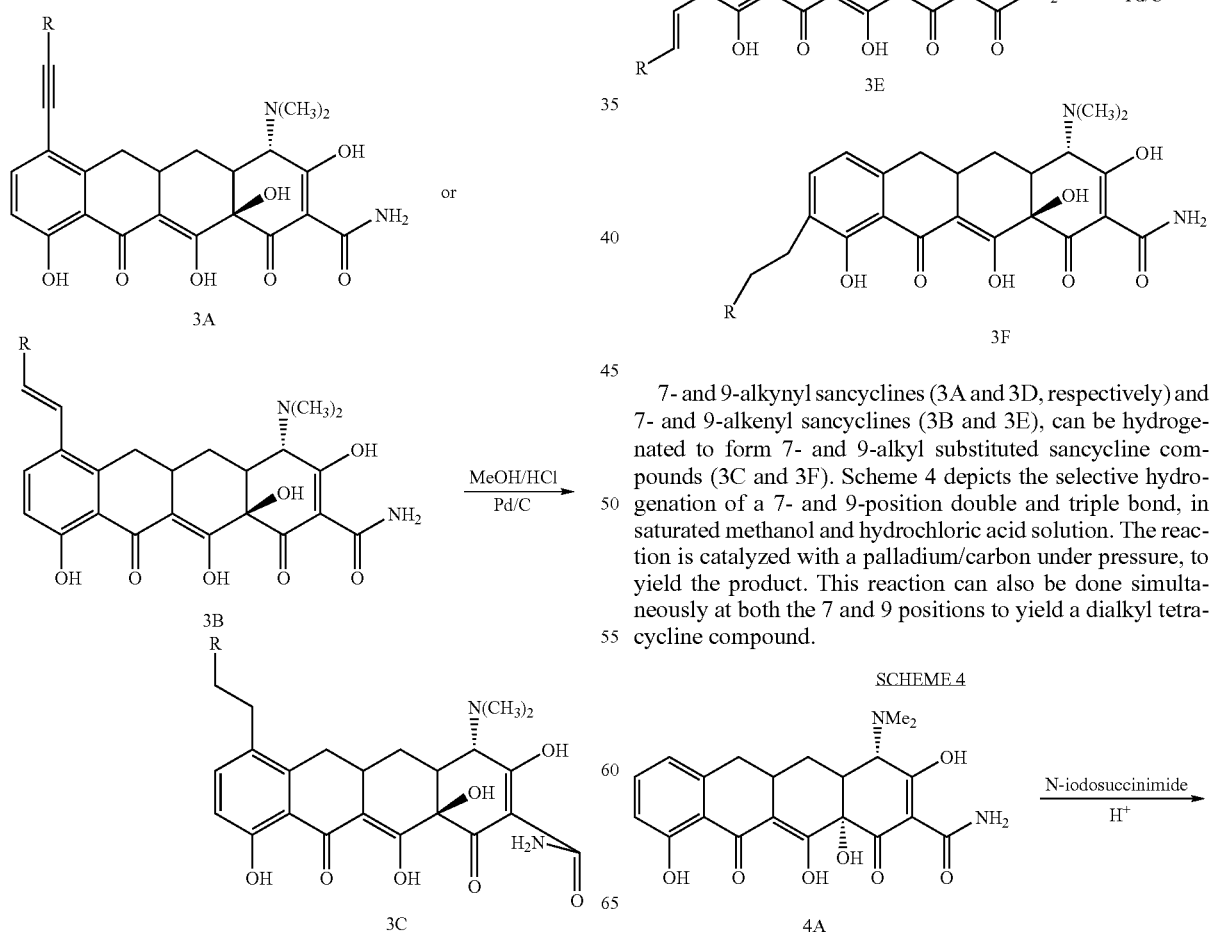

7- and 9-alkynyl sancyclines (3A and 3D, respectively) and 7- and 9-alkenyl sancyclines (3B and 3E), can be hydrogenated to form 7- and 9-alkyl substituted sancycline compounds (3C and 3F). Scheme 4 depicts the selective hydrogenation of a 7- and 9-position double and triple bond, in saturated methanol and hydrochloric acid solution. The reaction is catalyzed with a palladium/carbon under pressure, to yield the product. This reaction can also be done simultaneously at both the 7 and 9 positions to yield a dialkyl tetracycline compound.

SCHEME 4

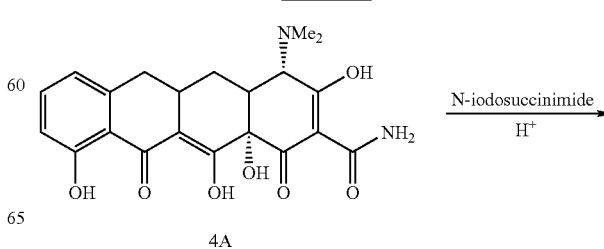

4A

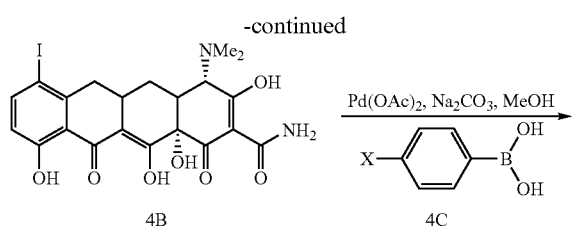

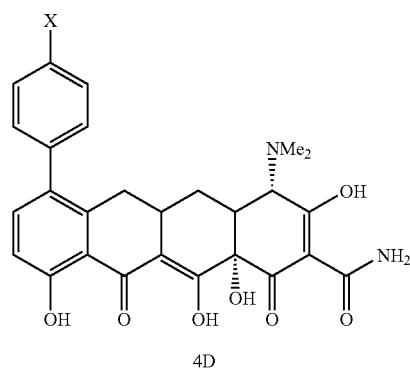

In Scheme 4, a general synthetic scheme for synthesizing 7-position aryl derivatives is shown. A Suzuki coupling of an aryl boronic acid with an iodosancycline compound is shown. An iodo sancycline compound (4B) can be synthesized from sancycline by treating sancycline (4A) with at least one equivalent N-iodosuccinimide (NIS) under acidic conditions. The reaction is quenched, and the resulting 7-iodo sancycline (4B) can then be purified using standard techniques known in the art. To form the aryl derivative, 7-iodo sancycline (4B) is treated with boronic acid (4C) plus aqueous sodium carbonate, and the reaction is catalyzed with palladium. The product (4D) can be purified by methods known in the art (such as HPLC). Other 7-aryl and alkynyl tetracycline compounds can be synthesized using similar protocols.

The 7,9-substituted tetracycline compounds of the invention can also be synthesized using Stille cross couplings. Stille cross couplings can be performed using an appropriate tin reagent (e.g., R—SnBu$_3$) and a halogenated tetracycline compound, (e.g., 7-iodosancycline). The tin reagent and the iodosancycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

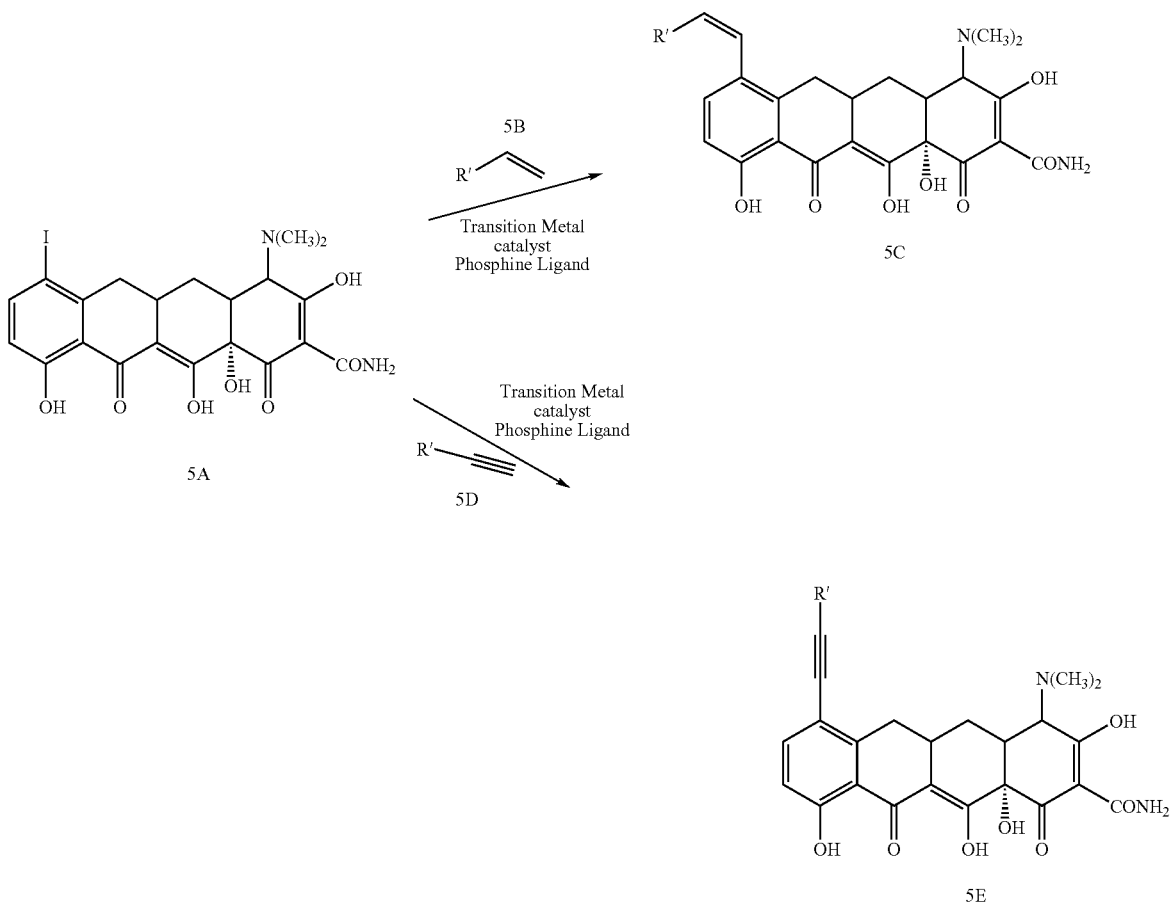

The compounds of the invention can also be synthesized using Heck-type cross coupling reactions. As shown in Scheme 5, Heck-type cross-couplings can be performed using a halogenated tetracycline compound (e.g., 7-iodosancycline, 5A), a reactive alkene (5B) or alkyne (5D), and an appropriate palladium or other transition metal catalyst. The resulting 7-substituted alkenyl (5C) or 7-substituted alkynyl (5E) tetracycline compound can then be purified using techniques known in the art.

Other substituted tetracycline compounds of the invention can be synthesized by using one or more of the following synthetic methods at either the 7- or 9-position, followed by the same or different chemistry at the other position. For example, if a group was placed at the 7-position, any of the above reaction methods could be used to further derivatize the 9-position, as shown in Example 1.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The invention also pertains to methods for treating a tetracycline responsive states in subjects, by administering to a subject an effective amount of a 7-substituted tetracycline compound of the invention (e.g., a compound of Formula (I) or shown in Table 1), such that the tetracycline responsive state is treated.

The language "tetracycline compound responsive state" includes states which can be treated, prevented, or otherwise ameliorated by the administration of a tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48:6686-6690 (1988)).

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., National Commission for Clinical Laboratory Standards, Document M7-A2, vol. 10, no. 8, pp. 13-20, 2$^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., K. pneumoniae, Salmonella, E. hirae, A. baumanii, B. catarrhalis, H influenzae, P. aeruginosa, E. faecium, E. coli, S. aureus or E. faecalis. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a tetracycline compound (e.g., a compound of Formula 1, Table 2, or other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below, with modifications to the procedure below within the skill of those of ordinary skill in the art.

Example 1

Synthesis of Compounds of the Invention 7,9-Diiodosancyline 30.0 mL of concentrated sulfuric acid was added to 1.00 g of sancycline hydrochloride hemihydrate with stirring and the solution cooled to 0° C. 1.09 g of N-iodosuccinimide was added portionwise to the solution over one hr and the reaction mixture monitored by HPLC and TLC. The reaction mixture was poured into 250 mL of ice water, extracted three times with n-butanol, and the solvent removed under reduced pressure. The crude residue was purified by preparative HPLC yielding 787 mg (61%) of 7-iodosancycline and 291 mg (22%) of 7,9-diiodosancycline as yellow and dark yellow crystals respectively.

MS (FAB): m/z 667 (M+H)

$^1$H NMR (Methanol d-4, 300 MHz) δ 8.35 (s, 1H), 3.78 (s, 1H), 3.33 (s, 2H), 2.88 (s, 7H), 2.41 (m, 2H), 1.41 (m, 5H).

Compound HZ
(7,9-Bis(3,4-Methylenedioxyphenyl)-Sancycline)

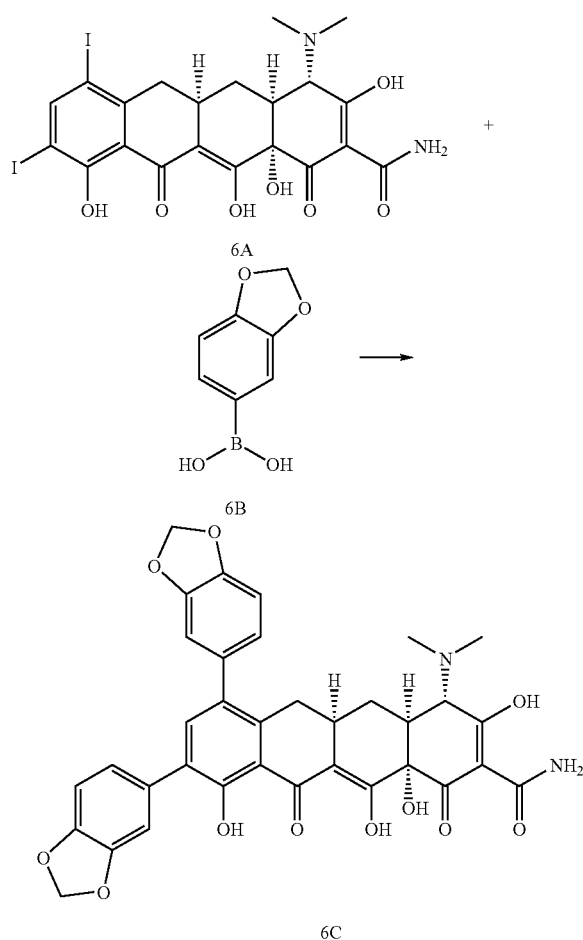

577 mg (0.74 mmol) 7,9-diiodo sancycline (6C) and 8.3 mg (0.37 mmol) palladium acetate were dissolved in 25 ml methanol, under a nitrogen atmosphere. The solution was warmed to 60° C. After stirring for ten minutes 234 mg (2.22 mmol), sodium carbonate was added followed by 246 mg (1.48 mmol) of 3,4-methylenedioxyphenyl boronic acid (6B). The reaction was complete in 4 hours. The reaction mixture was filtered through a celite bed and concentrated under reduced pressure. This crude product was purified by preparative liquid chromatography using a $C_{18}$ stationary phase with eluent A: 0.1% TFA in water and eluent B: 0.1% TFA in acetonitrile. 60 mg pure product was isolated (6C).

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal., filtering through Celite, and subsequent removal of the solvent in vacuo to produce the 7-isomer compound as a pure yellow solid in 75% yield.

MS (M+H) (formic acid solvent) 541.3.

\Rt: Hypersil C18 BDS Column, 11.73

$^1$H NMR (Methanol $d_4$-300 MHz) δ 7.87-7.90 (d, 1H), 6.66-6.69 (d, 1H), 4.06 (s, 1H), 2.98 (s, 6H), 2.42 (m, 1H), 2.19 (m, 1H), 1.62 (m, 4H), 0.99 (m, 2H)

7-Tetramethylsilylethynyl-Sancycline

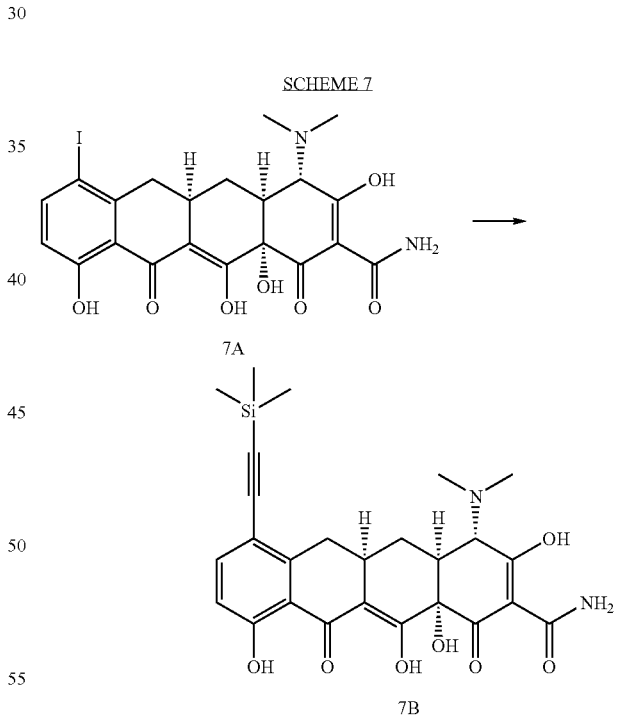

To a solution of 6.54 g (10 mmol) 7-iodo-sancycline trifluoroacetate 500 mg tetrakis-triphenylphosphino-palladate, 500 mg copper(I) iodide, 100 mg palladium acetate and 30 ml triethylamine 3 ml trimethylsilyl-acetylene was added. The reaction mixture was stirred at room temperature for two hours than filtered through a celite bed and concentrated. The dry material was picked up in methanol, the insolubles were filtered out. The solution was concentrated to recover 6.8 g of the product (7B).

7-Ethynyl-Sancycline

SCHEME 8

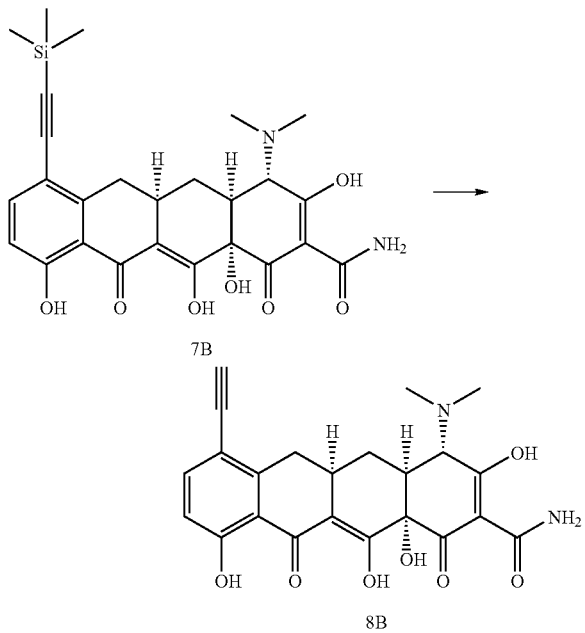

7-Tetramethylsilylethynyl-sancycline (7B) is dissolved in 300 ml methanol, and stirred at 40° C. with 6.8 g potassium carbonate. When no starting material could be detected by HPLC (~3 hours), the reaction mixture was cooled in an ice/water bath and solids were removed by filtration. The structure of the alkyne (8B) was confirmed by LCMS. 8B was then used without further purification in the next step.

7-Ethyl-Sancycline

SCHEME 9

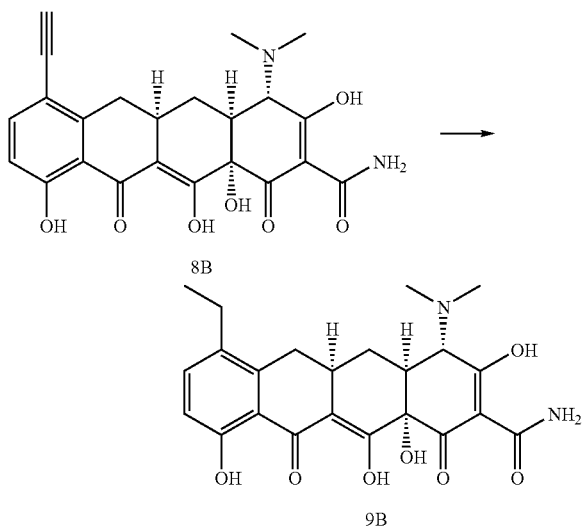

10% palladium catalyst on charcoal (1 g) was added to 7-ethynyl sancycline (8C) in a saturated methanol hydrochloric acid solvent. The mixture was placed in a hydrogenator under 50 psi hydrogen pressure. The reaction was completed in ~8 hours. The catalyst was filtered off, and the resulting solution was concentrated. The crude product was purified by preparative liquid chromatography using a $C_{18}$ stationary phase with eluent A: 0.1% TFA in water and eluent B: 0.1% TFA in acetonitrile. The combined clean fractions are concentrated and hydrochloric acid saturated isopropanol added. The pure product is precipitated by addition of diethylether and filtered off. After drying under reduced pressure 3.2 g of 7-ethyl-sancycline (9B) was isolated.

7-Ethyl-9-Iodo-Sancycline

SCHEME 10

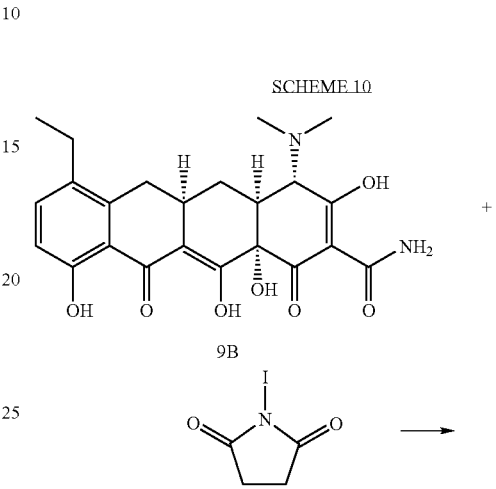

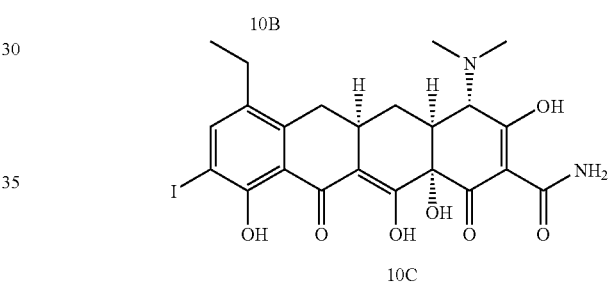

7-Ethyl-Sancycline (9B, 6.7 mmol, 3.2 g) was dissolved in 75 ml methanesulfonic acid at room temperature. N-iodo succinimide (10B, 13.5 mmol, 3.05 g) was added over two hours in 6 portions. After two hours diethyl ether was added, and the precipitate was filtered off and dried. The crude product was purified by preparative liquid chromatography using a $C_{18}$ stationary phase with eluent A: 0.1% TFA in water and eluent B: 0.1% TFA in acetonitrile. 1.5 g of pure product (10C) was isolated.

Compound HO
(7-Ethyl-9-Cyclohexenylethynyl-Sancycline)

SCHEME 11

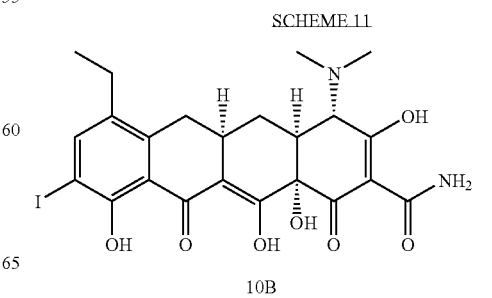

33

-continued

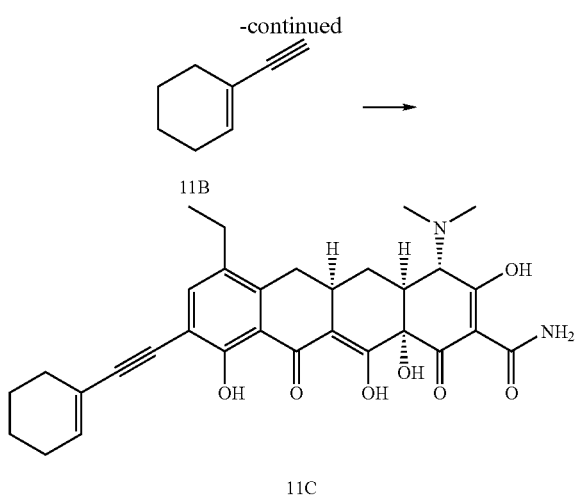

To a solution of 7-ethyl-sancycline (500 mg, 1.13 mmol), 50 mg tetrakis-triphenylphosphino-palladate, 50 mg copper (I) iodide, 10 mg palladium acetate and 3 ml triethylamine 0.1 ml cyclohexenyl-acetylene was added. The reaction mixture was stirred at 60° C. for one hour, filtered through a celite bed and concentrated. The dry material was dissolved in methanol and filtered. The solution was then concentrated and purified using preparative liquid chromatography. The preparative liquid chromatography used a $C_{18}$ stationary phase with eluent A: 0.1% TFA in water and eluent B: 0.1% TFA in acetonitrile. 100 mg of Compound HO was isolated.

7-iodo-9-t-Butyl-Sancycline

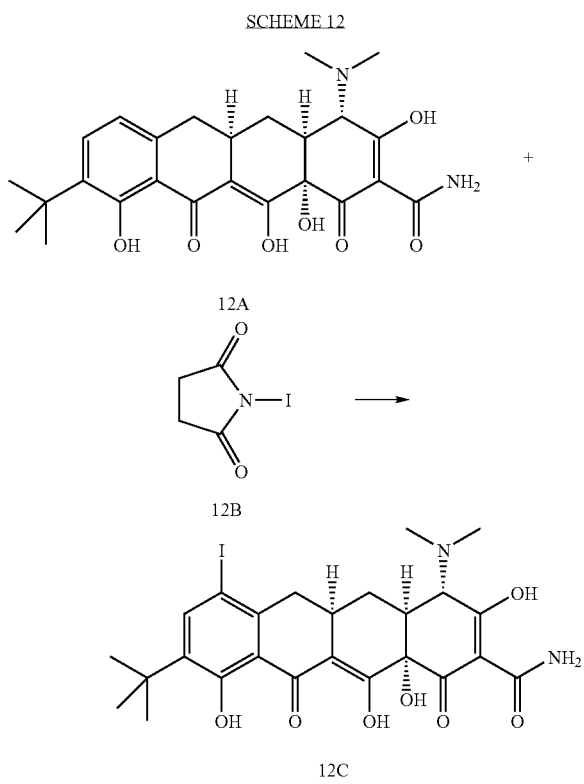

9-tbutyl-sancycline (12A, 1.13 g, 2 mmol) was dissolved in 5 ml methanesulfonic acid (0.448, 2 mmol). N-iodosuccinimide (12B) was added at room temperature over one hour in four portions. The product (12C) was precipitated with diethyl ether, filtered off and used in other reaction without further purification.

Compound ID (7-(2-Methoxy-5-Dimethylaminomethylphenyl)-9-t-Butyl-Sancycline

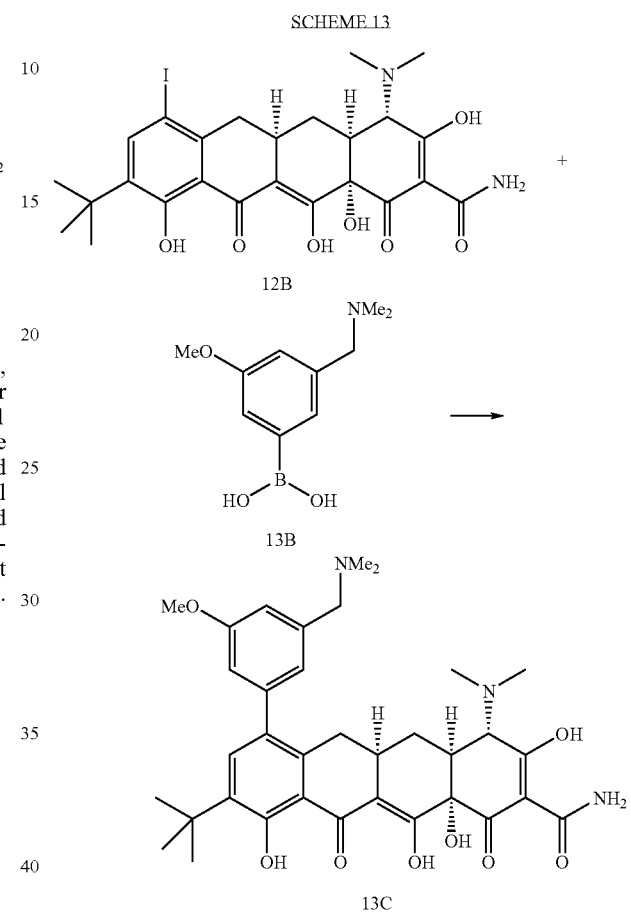

7-Iodo-9-t-butyl-sancycline (12B, 710 mg, 1.0 mmol) and palladium acetate (22.4 mg, 0.1 mmol) were dissolved in 25 ml of methanol under a nitrogen atmosphere. Cesium carbonate (3.25 g, 10 mmol) and 2-methoxy-5-dimethylaminomethylphenyl-boronic acid (13B, 0.435 g, 0.15 mmol) were added. The reaction mixture was stirred at 60° C. for two hours and then filtered through a celite bed and concentrated under reduced pressure. The crude product was purified by preparative liquid chromatography using a $C_{18}$ stationary phase with eluent A: 0.1% TFA in water and eluent B: 0.1% TFA in acetonitrile. 210 mg of Compound ID (13C) was isolated.

Example 2

In Vitro Minimum Inhibitory Concentration (MIC) Assay

The following assay is used to determine the efficacy of minocycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The minocycline compound solutions are diluted to 50 μL volumes, with a test compound concentration of 0.098 μg/ml. Optical density (OD) determinations are made from fresh log-phase broth cultures of the test strains.

Dilutions are made to achieve a final cell density of $1\times10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the minocycline compound that inhibits growth. Compounds of the invention indicate good inhibition of growth.

In Table 2, compounds which were good inhibitors of growth of a particular bacteria are indicated with *, compounds which were very good inhibitors of a particular bacteria are indicated with , and compounds with were particularly good inhibitors of a particular bacteria are indicated with *.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

TABLE 2

| ID | STRUCTURE | S. aureus | E. hirae | E. coli |
|---|---|---|---|---|
| HA | 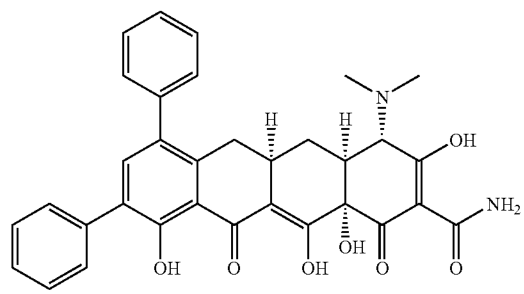 | NT | NT | NT |
| HB | 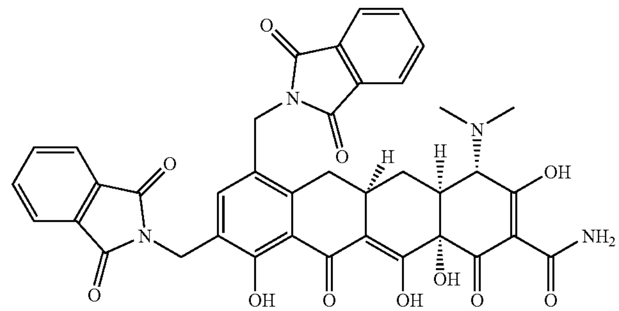 |  |  | * |
| HC | 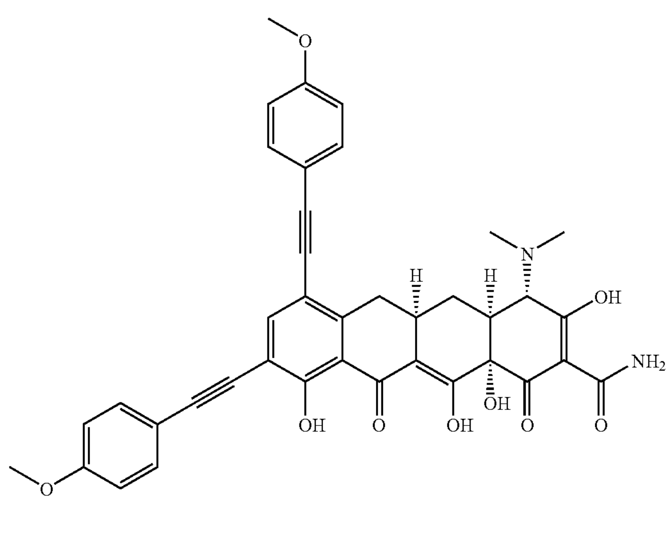 | * | * | * |

TABLE 2-continued
| ID | STRUCTURE | S. aureus | E. hirae | E. coli |
|---|---|---|---|---|
| HD | 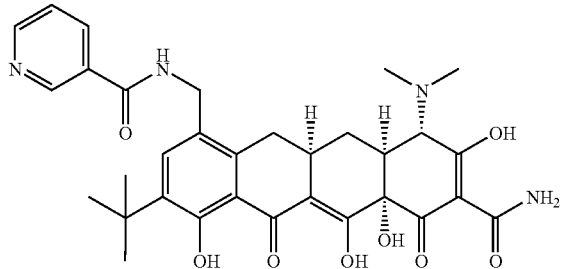 | NT | NT | NT |
| HE | 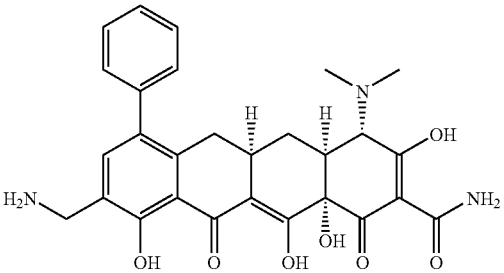 |  |  | * |
| HF | 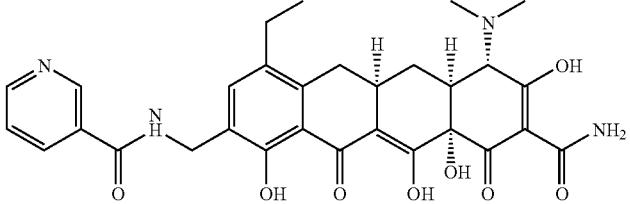 | * | ** | * |
| HG | 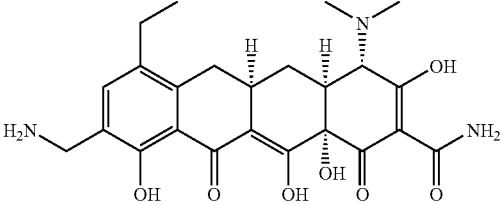 | ** | * | * |
| HI | 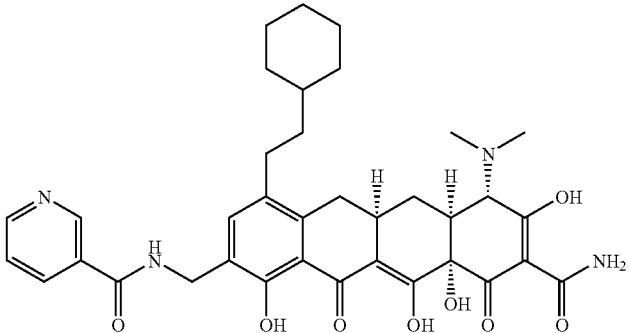 |  |  | * |

TABLE 2-continued

| ID | STRUCTURE | S. aureus | E. hirae | E. coli |
|---|---|---|---|---|
| HJ | 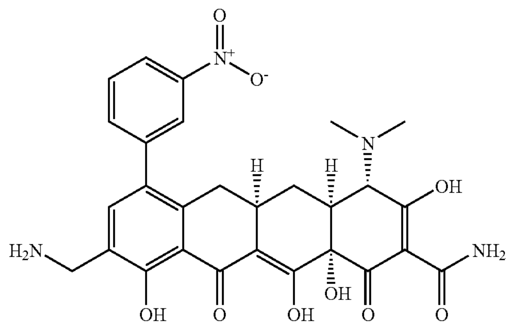 |  |  | * |
| HK | 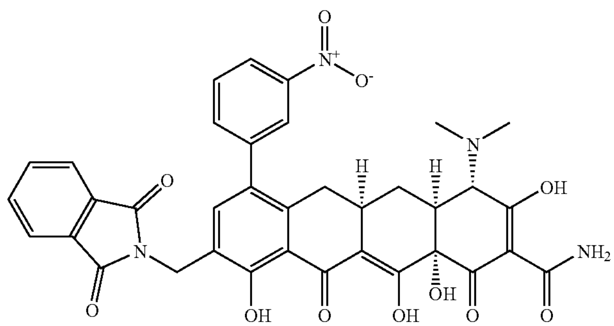 |  |  | * |
| HL | 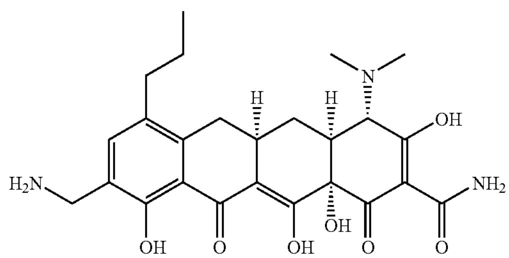 |  |  | ** |
| HM | 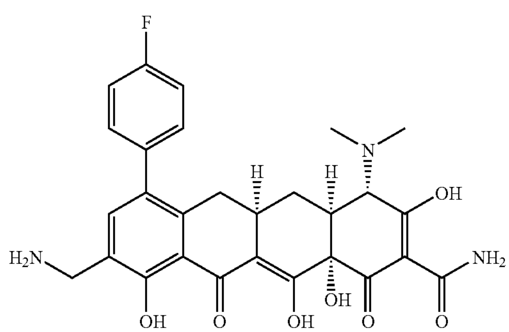 |  |  | ** |
| HN | 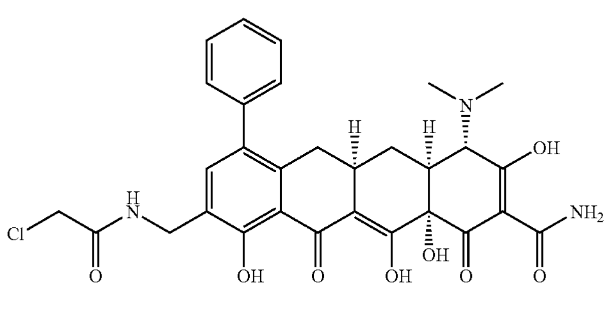 | * |  | * |

TABLE 2-continued

| ID | STRUCTURE | S. aureus | E. hirae | E. coli |
|----|-----------|-----------|----------|---------|
| HO | 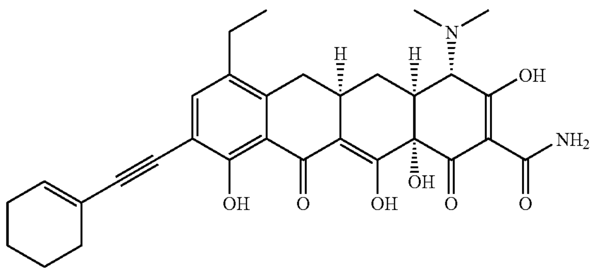 | * | * | * |
| HP | 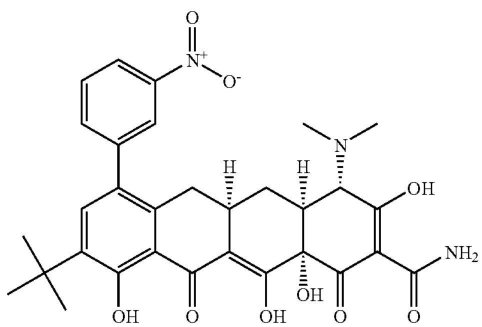 |  | * | * |
| HQ | 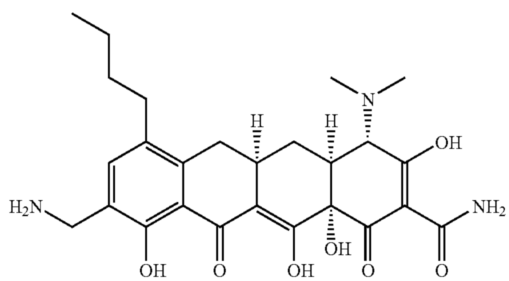 |  |  | ** |
| HR | 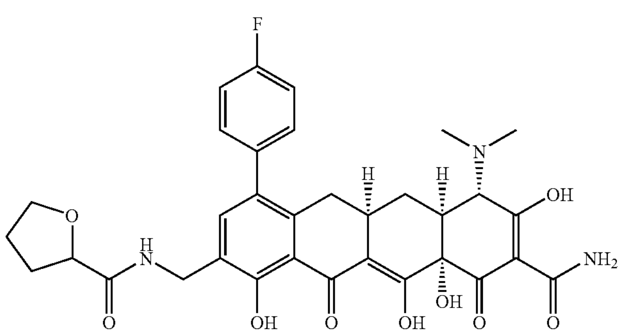 |  |  | * |
| HS | 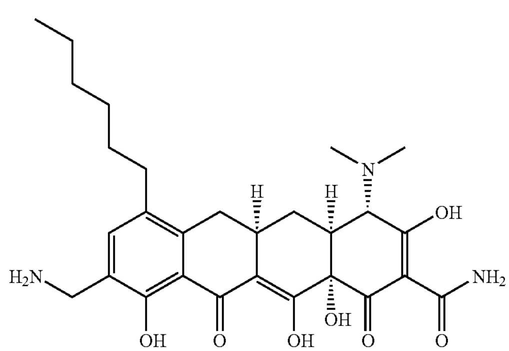 |  | * | *** |

TABLE 2-continued
| ID | STRUCTURE | S. aureus | E. hirae | E. coli |
|---|---|---|---|---|
| HT | 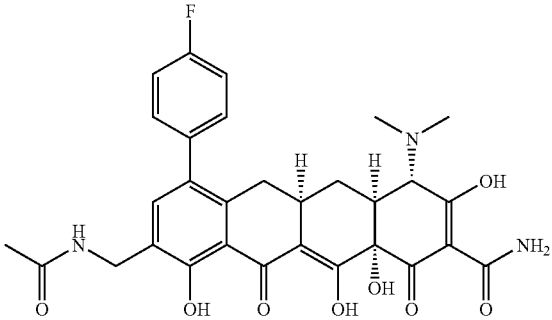 |  |  | * |
| HU | 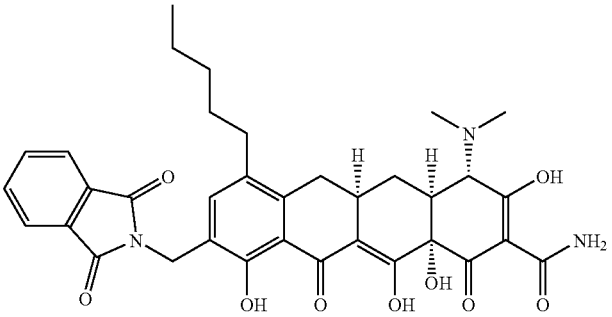 |  | * | * |
| HV | 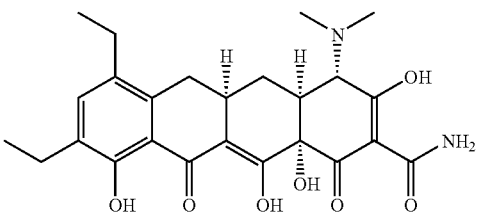 | * | * | ** |
| HW | 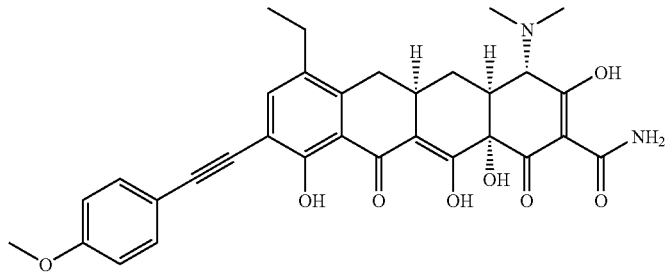 |  |  | * |
| HX | 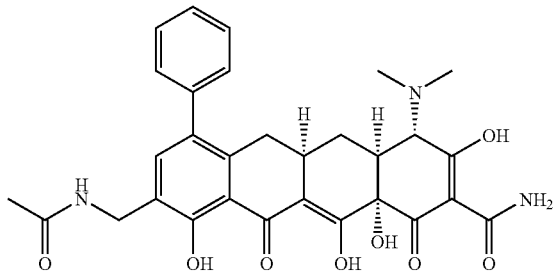 |  | * | * |

TABLE 2-continued

| ID | STRUCTURE | S. aureus | E. hirae | E. coli |
|---|---|---|---|---|
| HY | 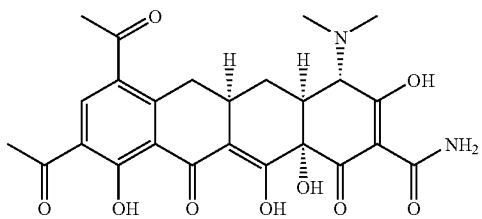 | NT | NT | NT |
| HZ | 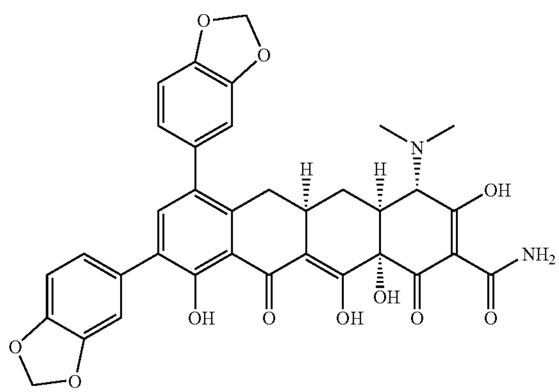 | * |  | * |
| IA | 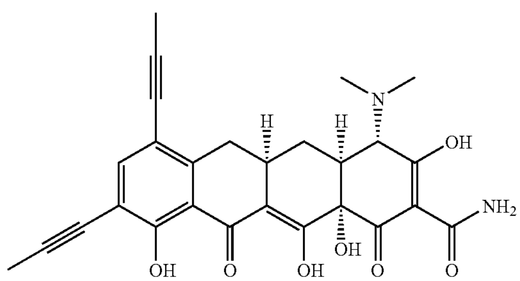 | * | * | * |
| IB | 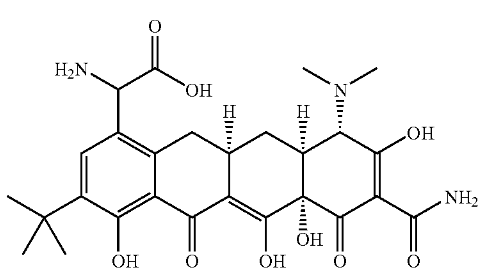 | NT | NT | NT |
| IC | 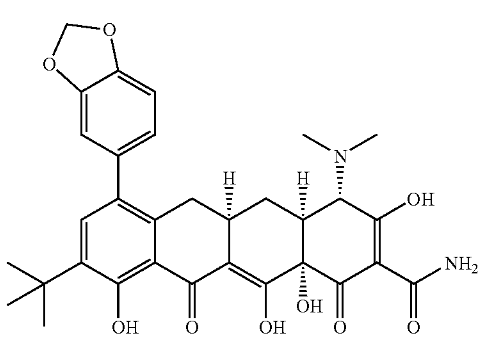 | NT | NT | NT |

TABLE 2-continued

| ID | STRUCTURE | S. aureus | E. hirae | E. coli |
|----|-----------|-----------|----------|---------|
| ID | 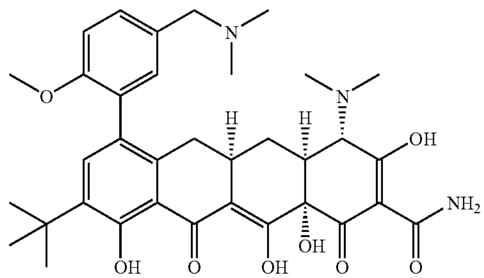 | NT | NT | NT |
| IE | 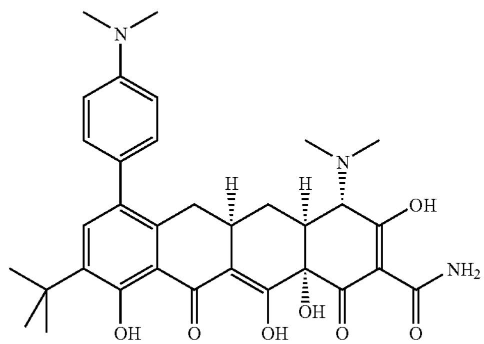 | NT | NT | NT |
| IF | 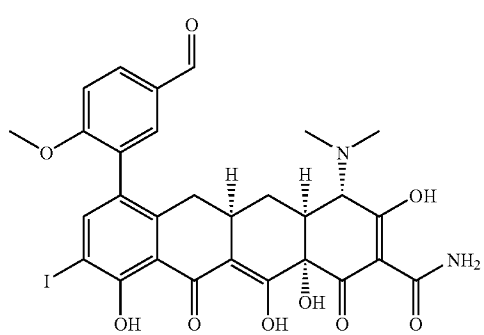 | NT | NT | NT |
| IG | 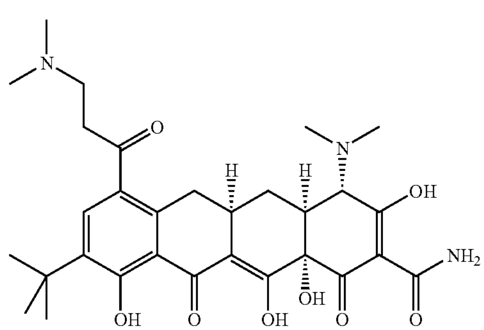 | NT | NT | NT |

TABLE 2-continued

| ID | STRUCTURE | S. aureus | E. hirae | E. coli |
|----|-----------|-----------|----------|---------|
| IH | 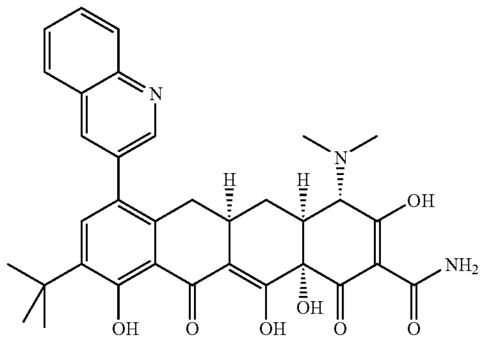 | NT | NT | NT |
| II | 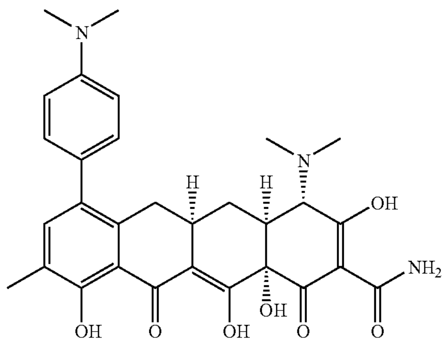 | NT | NT | NT |
| IJ | 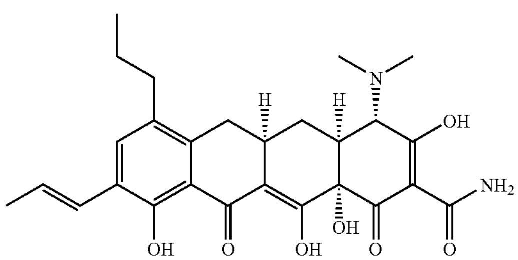 | NT | NT | NT |
| IK | 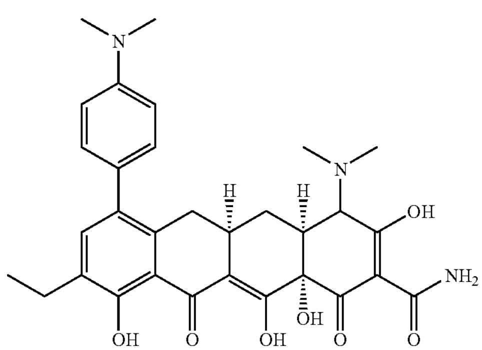 | NT | NT | NT |

TABLE 2-continued
| ID | STRUCTURE | S. aureus | E. hirae | E. coli |
|---|---|---|---|---|
| IL | 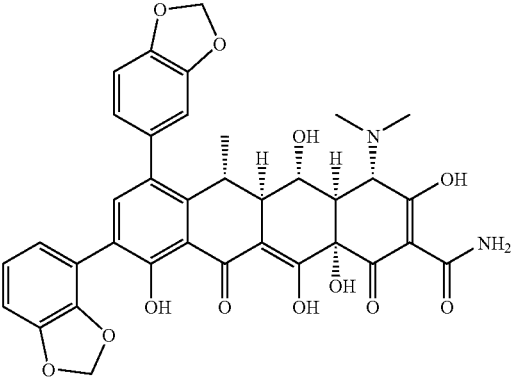 | NT | NT | NT |
| IM | 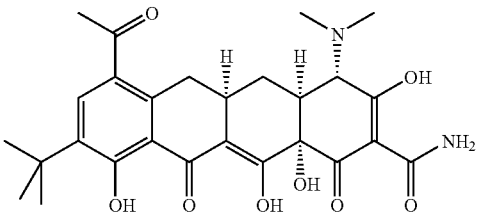 | NT | NT | NT |
| IN | 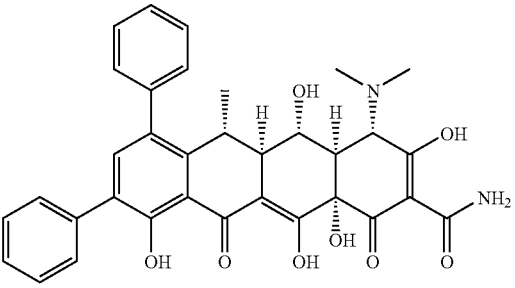 | NT | NT | NT |
| IO | 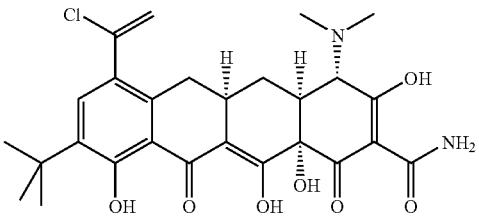 | NT | NT | NT |
| IP | 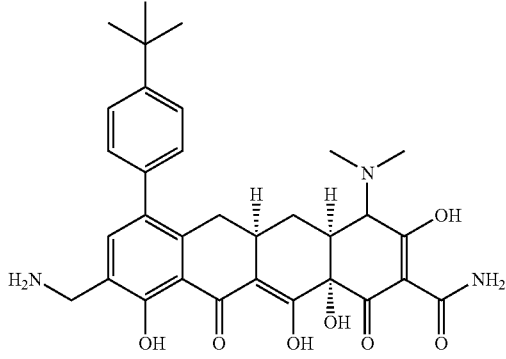 | NT | NT | NT |

TABLE 2-continued

| ID | STRUCTURE | S. aureus | E. hirae | E. coli |
|---|---|---|---|---|
| IQ | 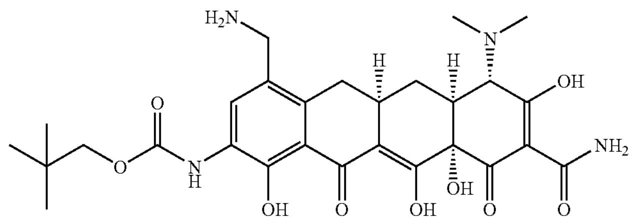 | NT | NT | NT |
| IR | 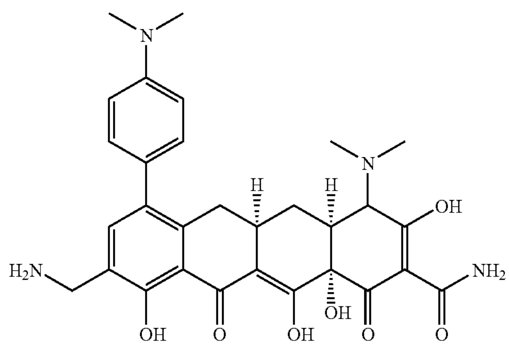 | NT | NT | NT |
| IS | 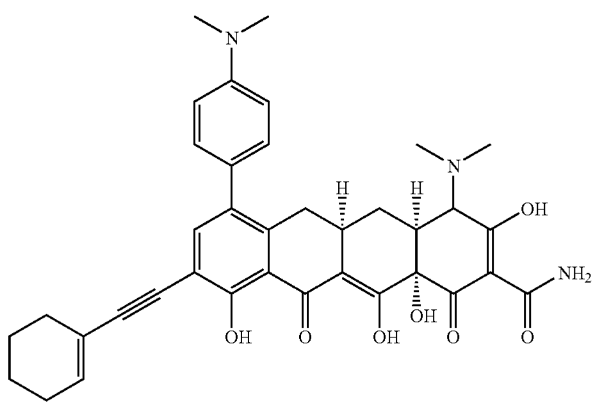 | NT | NT | NT |
| IT | 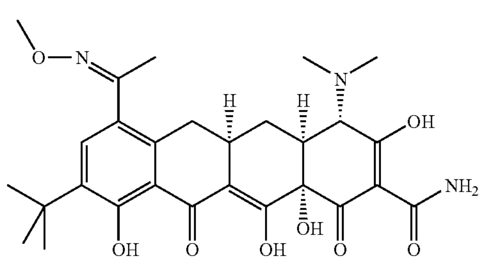 | NT | NT | NT |
| IU | 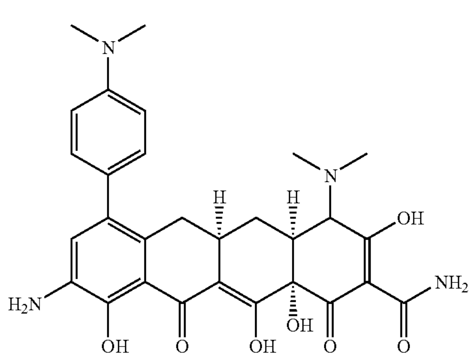 | NT | NT | NT |

TABLE 2-continued

| ID | STRUCTURE | S. aureus | E. hirae | E. coli |
|----|-----------|-----------|----------|---------|
| IV | 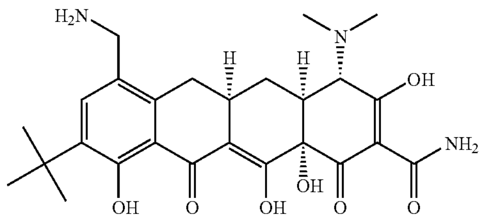 | NT | NT | NT |
| IW | 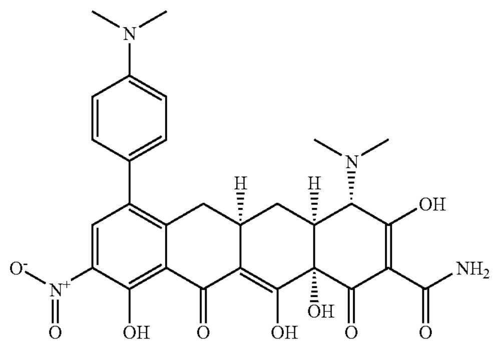 | NT | NT | NT |
| IX | 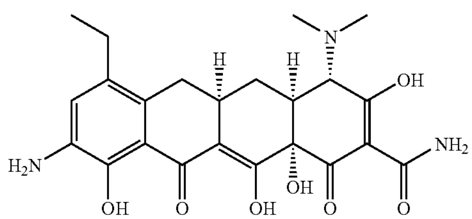 | NT | NT | NT |
| IY | 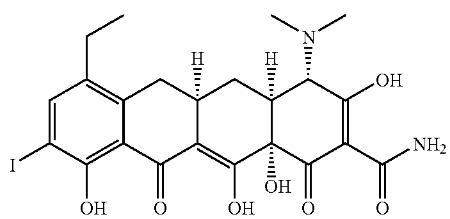 | NT | NT | NT |
| IZ | 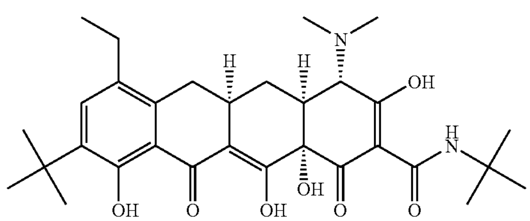 | NT | NT | NT |
| JA | 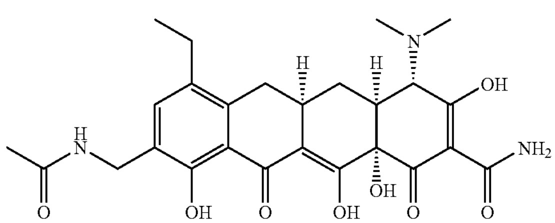 | NT | NT | NT |

TABLE 2-continued

| ID | STRUCTURE | S. aureus | E. hirae | E. coli |
|---|---|---|---|---|
| JB | 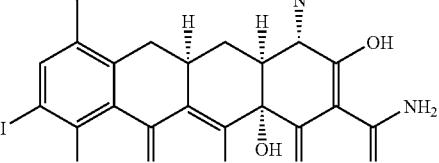 | NT | NT | NT |
| JC | 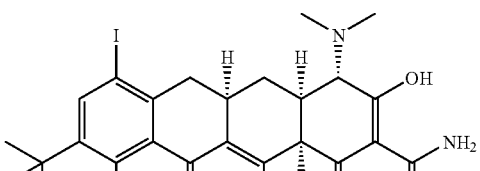 | NT | NT | NT |
| JD | 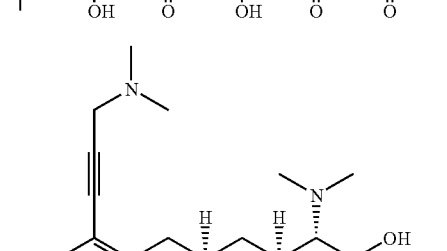 | NT | NT | NT |

The invention claimed is:

1. A 7,9-substituted tetracycline compound of Formula I:

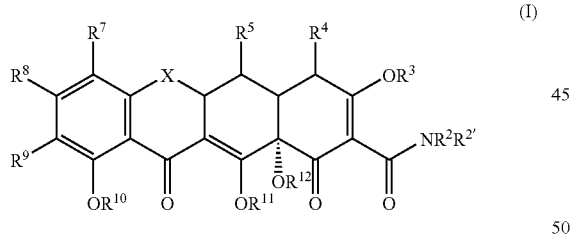

wherein:

X is CHC($R^{13}$Y'Y) or C$R^{6'}R^6$;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic or hetero aromatic;

$R^4$ is N$R^{4'}R^{4''}$, alkyl, alkenyl, alkynyl, hydroxyl or halogen;

$R^3$, $R^{10}$, $R^{11}$ and $R^{12}$ are each hydrogen;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;

$R^6$ and $R^{6'}$ are each independently hydrogen, methylene, hydroxyl, halogen, thiol, alkyl, alkenyl, alkynyl, aryl, alkoxy, alkylthio, alkylsulfinyl, alkylsulfonyl, alkylamino or arylalkyl;

$R^7$ is phenyl, pyrrole, thiophene, thiazole, isothiazole, imidazole, triazole, tetrazole, pyrazole, oxazole, isooxazole, pyridine, pyridazine, pyrimidine, naphthalene, benzoxazole, benzodioxazole, benzothiazole, benzoimidazole, benzothiophene, methylenedioxyphenyl, quinoline, isoquinoline, naphthridine, indole, benzofuran, purine, deazapurine or indolizine;

$R^9$ is nitro, alkyl, alkenyl, heteroaryl, alkoxy, alkylthio, alkylsulfinyl, alkylsulfonyl, arylalkyl, amino, arylalkenyl, arylalkynyl, thionitroso or —(CH$_2$)$_{0-3}$N$R^{9c}$C(=Z')Z$R^{9a}$;

Z is C$R^{9d}R^{9e}$, S, N$R^{9b}$ or O;

Z' is O or S;

$R^{9a}$, $R^{9b}$, $R^{9c}$, $R^{9d}$ and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic or heteroaromatic;

$R^8$ is hydrogen;

$R^{13}$ is hydrogen, hydroxy, alkyl, alkenyl, alkynyl, alkoxy, alkylthio, alkylsulfinyl, alkylsulfonyl, alkylamino or arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino or arylalkyl, or pharmaceutically acceptable salts or esters thereof.

2. The tetracycline compound of claim 1, wherein X is $CR^6R^{6'}$; $R^2$, $R^{2'}$, $R^6$, $R^{6'}$, $R^{10}$, $R^{11}$ and $R^{12}$ are each hydrogen; $R^4$ is $NR^{4'}R^{4''}$; $R^{4'}$ and $R^{4''}$ are lower alkyl; and $R^5$ is hydroxy or hydrogen.

3. The tetracycline compound of claim 2, wherein $R^{4'}$ and $R^{4''}$ are each methyl and $R^5$ is hydrogen.

4. The tetracycline compound of claim 1, wherein $R^7$ is substituted or unsubstituted phenyl.

5. The tetracycline compound of claim 4, wherein said phenyl is substituted with one or more substituents selected from the group consisting of alkyl, alkenyl, halogen, hydroxyl, alkoxy, alkylcarbonyloxy, arylcarbonyloxy, alkoxycarbonylamino, alkoxycarbonyloxy, aryloxycarbonyloxy, carboxylate, alkylcarbonyl, alkylaminocarbonyl, arylalkyl aminocarbonyl, alkenylaminocarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, azido, heterocyclyl, alkylaryl, aryl and heteroaryl.

6. The tetracycline compound of claim 5, wherein said substituent is substituted or unsubstituted alkyl, nitro, halogen, amino or alkoxy.

7. The tetracycline compound of claim 6, wherein said halogen substituent is fluorine.

8. The tetracycline compound of claim 6, wherein said alkoxy substituent is methylenedioxy or methoxy.

9. The tetracycline compound of claim 5, wherein said amino substituent is dialkylamino.

10. The tetracycline compound of claim 4, wherein $R^7$ is unsubstituted phenyl.

11. The tetracycline compound of claims 1, wherein $R^9$ is substituted or unsubstituted alkyl.

12. The tetracycline compound of claim 11, wherein said alkyl is substituted with one or more substituents selected from the group consisting of alkenyl, halogen, hydroxyl, alkoxy, alkylcarbonyloxy, arylcarbonyloxy, arylcarbonylamino, alkoxycarbonylamino, alkoxycarbonyloxy, aryloxycarbonyloxy, alkylcarbonylamino, carboxylate, alkylcarbonyl, alkylaminocarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, azido, heterocyclyl, alkylaryl, aryl and heteroaryl.

13. The tetracycline compound of claim 12, wherein said substituent is unsubstituted amino.

14. The tetracycline compound of claim 1, wherein said tetracycline compound is:

[chemical structure]

or pharmaceutically acceptable salts thereof.

15. A 7,9-substituted tetracycline compound of Formula I:

[chemical structure] (I)

wherein:
X is $CHC(R^{13}Y'Y)$ or $CR^{6'}R^6$;
$R^2$, $R^{2'}$, $R^{4'}$ and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic or heteroaromatic;
$R^4$ is hydrogen;
$R^3$, $R^{10}$, $R^{11}$ and $R^{12}$ are each hydrogen;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;
$R^6$ and $R^{6'}$ are each independently hydrogen, methylene, hydroxyl, halogen, thiol, alkyl, alkenyl, alkynyl, aryl, alkoxy, alkylthio, alkylsulfinyl, alkylsulfonyl, alkylamino or arylalkyl;
$R^7$ is aryl;
$R^9$ is nitro, alkyl, alkoxy, alkylthio, alkylsulfinyl, alkylsulfonyl, arylalkyl, amino, arylalkenyl, arylalkynyl, thionitroso or $-(CH_2)_{0-3}NR^{9c}C(=Z')ZR^{9a}$;
Z is $CR^{9d}R^{9e}$, S, $NR^{9b}$ or O;
Z' is O or S;
$R^{9a}$, $R^{9b}$, $R^{9c}$, $R^{9d}$ and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic or heteroaromatic;
$R^8$ is hydrogen;
$R^{13}$ is hydrogen, hydroxy, alkyl, alkenyl, alkynyl, alkoxy, alkylthio, alkylsulfinyl, alkylsulfonyl, alkylamino or arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino or arylalkyl, or pharmaceutically acceptable salts or esters thereof.

16. A 7,9-substituted tetracycline compound of Formula I:

[chemical structure] (I)

wherein:
X is $CHC(R^{13}Y'Y)$ or $CR^{6'}R^6$;
$R^2$, $R^{2'}$, $R^{4'}$ and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic or heteroaromatic;

$R^4$ is $NR^{4'}R^{4''}$ alkyl, alkenyl, alkynyl, hydroxyl or halogen;

$R^3$, $R^{10}$, $R^{11}$ and $R^{12}$ are each hydrogen;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;

$R^6$ and $R^{6'}$ are each independently hydrogen, methylene, hydroxyl, halogen, thiol, alkyl, alkenyl, alkynyl, aryl, alkoxy, alkylthio, alkylsulfinyl, alkylsulfonyl, alkylamino or arylalkyl;

$R^7$ is pyrrole, thiophene, thiazole, isothiazole, imidazole, triazole, tetrazole, pyrazole, oxazole, isooxazole, pyridine, pyridazine, pyrimidine, naphthalene, benzoxazole, benzodioxazole, benzothiazole, benzoimidazole, benzothiophene, methylenedioxyphenyl, quinoline, isoquinoline, naphthridine, indole, benzofuran, purine, deazapurine or indolizine;

$R^9$ is substituted phenyl;

$R^8$ is hydrogen;

$R^{13}$ is hydrogen, hydroxy, alkyl, alkenyl, alkynyl, alkoxy, alkylthio, alkylsulfinyl, alkylsulfonyl, alkylamino or arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino or arylalkyl, or pharmaceutically acceptable salts or esters thereof.

17. A tetracycline compound selected from the group consisting of:

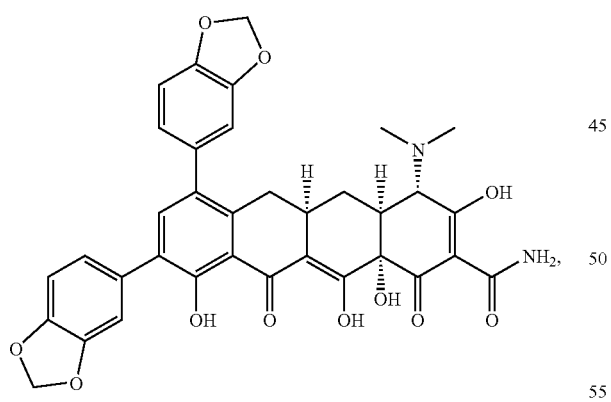

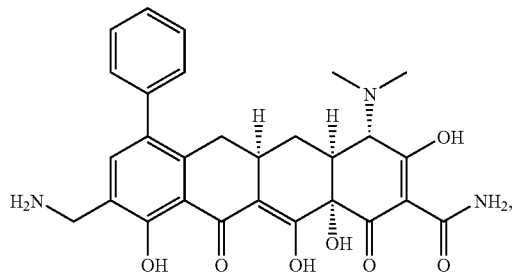

-continued

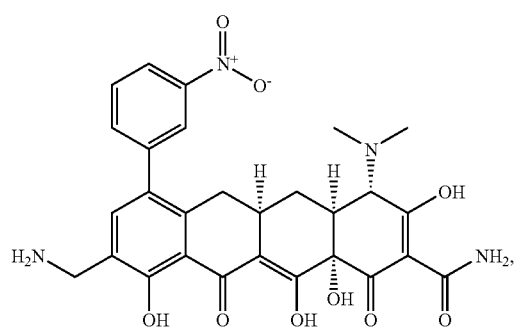

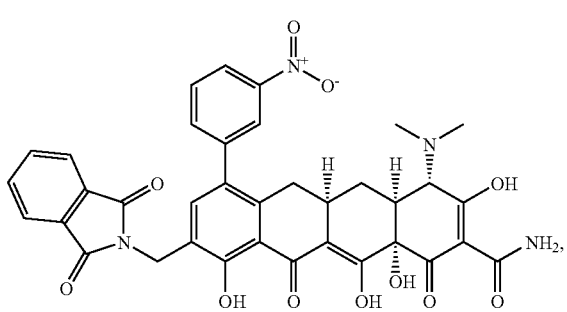

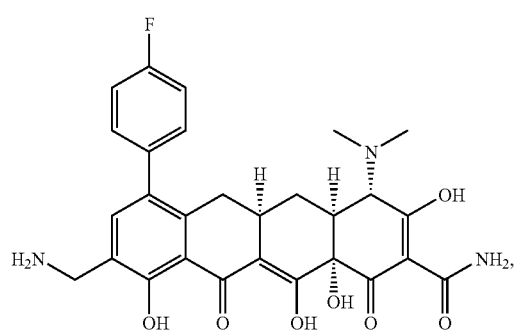

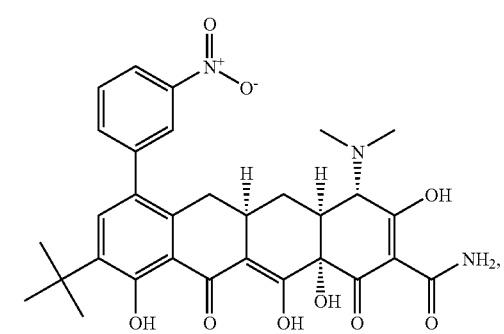

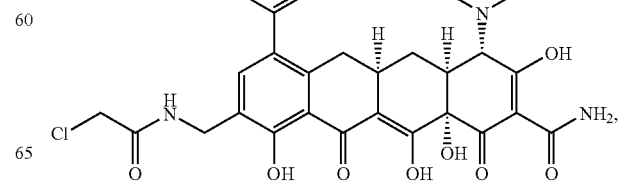

-continued
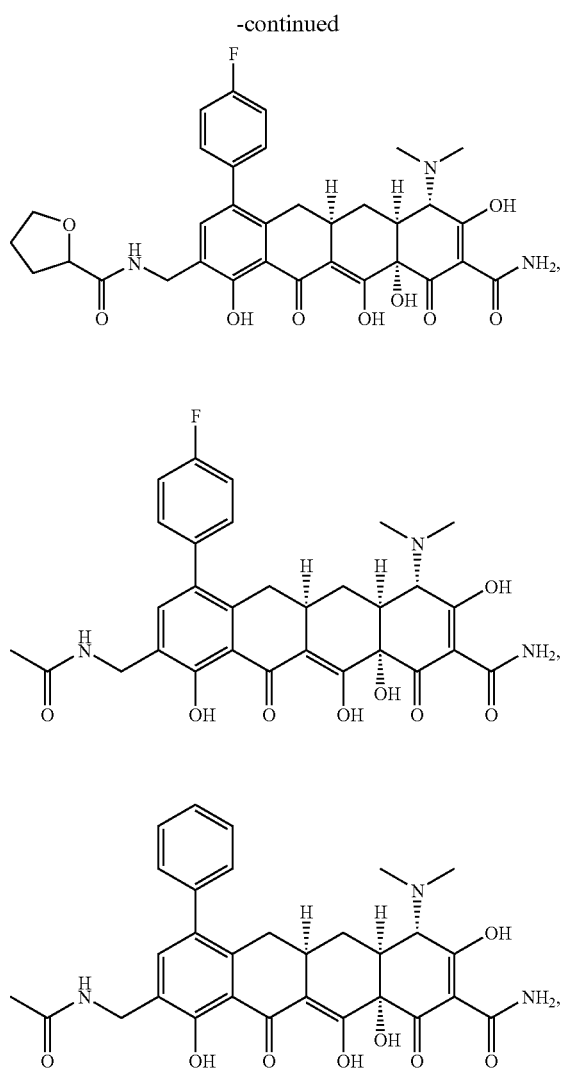
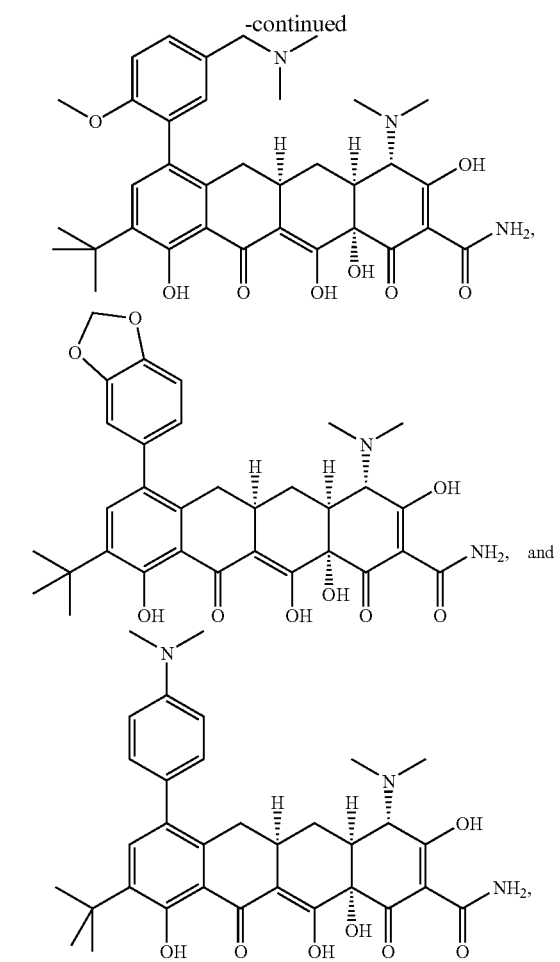
or pharmaceutical acceptable salts thereof.
18. A pharmaceutical composition comprising a therapeutically effective amount of a tetracycline compound of claim 1, and a pharmaceutically acceptable carrier.
* * * * *